US009295823B2

(12) United States Patent
Rykhus, Jr. et al.

(10) Patent No.: US 9,295,823 B2
(45) Date of Patent: Mar. 29, 2016

(54) NEEDLELESS INJECTION DEVICE COMPONENTS, SYSTEMS, AND METHODS

(76) Inventors: Robert L. Rykhus, Jr., Minnetonka, MN (US); Jason W. Ogdahl, Minnetonka, MN (US); Justin M. Crank, Minnetonka, MN (US)

( * ) Notice: Subject to any disclaimer, the term of this patent is extended or adjusted under 35 U.S.C. 154(b) by 453 days.

(21) Appl. No.: 12/839,682

(22) Filed: Jul. 20, 2010

(65) Prior Publication Data

US 2011/0015614 A1 Jan. 20, 2011

Related U.S. Application Data

(63) Continuation-in-part of application No. PCT/US2009/006384, filed on Dec. 4, 2009.

(60) Provisional application No. 61/139,974, filed on Dec. 22, 2008, provisional application No. 61/122,808, filed on Dec. 16, 2008, provisional application No. 61/122,793, filed on Dec. 16, 2008, provisional application No. 61/226,864, filed on Jul. 20, 2009, provisional application No. 61/226,840, filed on Jul. 20, 2009, provisional application No. 61/226,844, filed on Jul. 20, 2009.

(51) Int. Cl.
*A61M 31/00* (2006.01)
*A61B 1/00* (2006.01)
*A61B 17/02* (2006.01)
*A61M 25/10* (2013.01)
*A61B 17/00* (2006.01)
*A61B 17/22* (2006.01)

(52) U.S. Cl.
CPC .............. *A61M 31/00* (2013.01); *A61B 1/0014* (2013.01); *A61B 1/00087* (2013.01); *A61B 17/0218* (2013.01); *A61M 25/1034* (2013.01); *A61B 2017/00296* (2013.01); *A61B 2017/00557* (2013.01); *A61B 2017/22069* (2013.01); *A61M 2025/1054* (2013.01); *A61M 2025/1081* (2013.01); *A61M 2210/1078* (2013.01)

(58) Field of Classification Search
CPC .......... A61M 25/10; A61M 2025/105; A61M 25/1018; A61M 2025/1065; A61M 31/00; A61M 25/1034; A61B 1/00082; A61B 17/12136; A61B 17/0218; A61B 1/0014
USPC .............................. 604/103, 103.03, 103.04
See application file for complete search history.

(56) References Cited

U.S. PATENT DOCUMENTS 4,093,108 A 6/1978 Hein et al.
4,130,119 A 12/1978 Sessions et al.
(Continued)

FOREIGN PATENT DOCUMENTS

EP 1929929 6/2008
WO WO9616606 A1 6/1996
(Continued)

*Primary Examiner* — Bhisma Mehta
*Assistant Examiner* — Bradley Osinski
(74) *Attorney, Agent, or Firm* — Kagan Binder, PLLC

(57) ABSTRACT

Described are needleless injection systems and methods that involve features including one or more of a tissue tensioner and a fitting that includes or attaches to a shaft, exemplary embodiments including: an elastic sleeve sized to fit under tension about the distal end of a flexible scope, such as an endoscope; a non-metal, polymeric tube-like device being optionally attached to the elastic sleeve for delivering a therapeutic fluid to a treatment site within a patient wherein the elastic sleeve may include an integral balloon (tissue tensioner) feature that can be used to position the injection orifice of the tube-like device proximate a treatment area.

17 Claims, 17 Drawing Sheets

(56) References Cited

U.S. PATENT DOCUMENTS

| | | | |
|---|---|---|---|
| 4,323,071 A * | 4/1982 | Simpson et al. | 606/194 |
| 4,742,817 A | 5/1988 | Kawashima et al. | |
| 4,946,442 A | 8/1990 | Sanagi | |
| 5,007,897 A | 4/1991 | Kalb | |
| 5,116,313 A | 5/1992 | McGregor | |
| 5,261,889 A | 11/1993 | Laine et al. | |
| 5,336,178 A | 8/1994 | Kaplan et al. | |
| 5,484,408 A * | 1/1996 | Burns | 604/102.02 |
| 5,571,161 A | 11/1996 | Starksen | |
| 5,693,016 A | 12/1997 | Gumaste et al. | |
| 5,840,062 A | 11/1998 | Gumaste et al. | |
| 6,203,533 B1 | 3/2001 | Ouchi | |
| 6,210,378 B1 | 4/2001 | Ouchi | |
| 6,238,336 B1 | 5/2001 | Ouchi | |
| 6,280,413 B1 | 8/2001 | Clark et al. | |
| 6,400,980 B1 | 6/2002 | Lemelson | |
| 6,537,205 B1 | 3/2003 | Smith | |
| 6,547,767 B1 | 4/2003 | Moein | |
| 6,605,037 B1 | 8/2003 | Moll | |
| 6,641,553 B1 | 11/2003 | Chee et al. | |
| 6,663,589 B1 * | 12/2003 | Halevy | 604/96.01 |
| 6,905,475 B2 | 6/2005 | Hauschild et al. | |
| 6,972,005 B2 * | 12/2005 | Boehm et al. | 604/191 |
| 7,329,236 B2 * | 2/2008 | Kesten et al. | 604/96.01 |
| 7,749,156 B2 | 7/2010 | Ouchi | |
| 8,460,179 B2 * | 6/2013 | Ikeda et al. | 600/115 |
| 2003/0163111 A1 | 8/2003 | Daellenbach | |
| 2004/0030320 A1 | 2/2004 | Chee et al. | |
| 2004/0162528 A1 | 8/2004 | Horvath et al. | |
| 2005/0159645 A1 | 7/2005 | Bertolero | |
| 2005/0192530 A1 | 9/2005 | Castellano | |
| 2005/0228225 A1 | 10/2005 | Hauschild et al. | |
| 2006/0129125 A1 | 6/2006 | Copa et al. | |
| 2007/0167921 A1 | 7/2007 | Burren et al. | |
| 2007/0225554 A1 | 9/2007 | Maseda et al. | |
| 2007/0244361 A1 | 10/2007 | Ikeda | |
| 2008/0114203 A1 | 5/2008 | Crank | |
| 2008/0119784 A1 | 5/2008 | Roychowdhury | |
| 2008/0119823 A1 | 5/2008 | Crank | |
| 2009/0124974 A1 | 5/2009 | Crank et al. | |
| 2009/0312696 A1 | 12/2009 | Copa et al. | |

FOREIGN PATENT DOCUMENTS

| | | |
|---|---|---|
| WO | WO9736625 A1 | 10/1997 |
| WO | WO0040279 A1 | 7/2000 |
| WO | WO0066199 A1 | 11/2000 |
| WO | WO0136029 A1 | 5/2001 |
| WO | WO0207812 A2 | 1/2002 |
| WO | WO03080155 | 10/2003 |
| WO | WO2004071612 A2 | 8/2004 |
| WO | WO2005094921 A1 | 10/2005 |
| WO | WO2006057604 A1 | 6/2006 |
| WO | WO2006063180 A2 | 6/2006 |
| WO | WO2006076699 A1 | 7/2006 |
| WO | WO2006084821 A2 | 8/2006 |
| WO | WO2006086719 A2 | 8/2006 |
| WO | WO2007038591 A2 | 4/2007 |
| WO | WO2007079152 A2 | 7/2007 |
| WO | WO2007136599 | 11/2007 |
| WO | WO2009134686 | 11/2009 |
| WO | WO2010046891 | 4/2010 |
| WO | WO2010065126 A2 | 6/2010 |
| WO | WO2010065127 A2 | 6/2010 |
| WO | WO2010651332 A2 | 6/2010 |
| WO | WO2010077271 A2 | 7/2010 |
| WO | WO2010747052 A2 | 7/2010 |
| WO | WO2011011382 | 1/2011 |
| WO | WO2011011392 | 1/2011 |
| WO | WO2011011396 | 1/2011 |
| WO | WO2011011406 | 1/2011 |
| WO | WO2011011423 A1 | 1/2011 |

\* cited by examiner

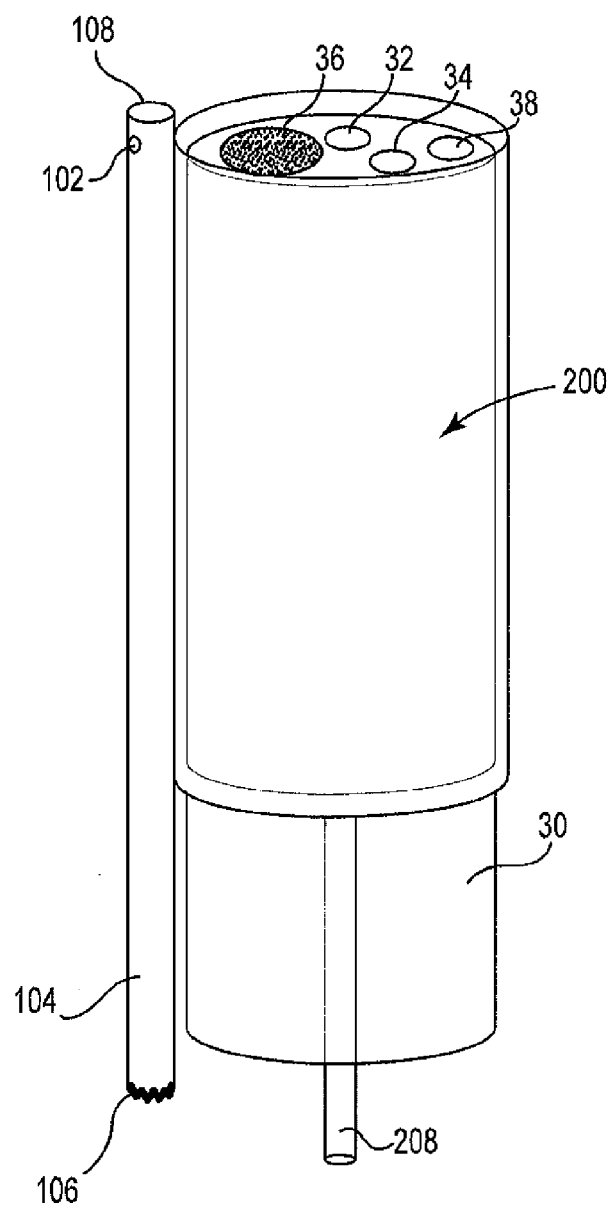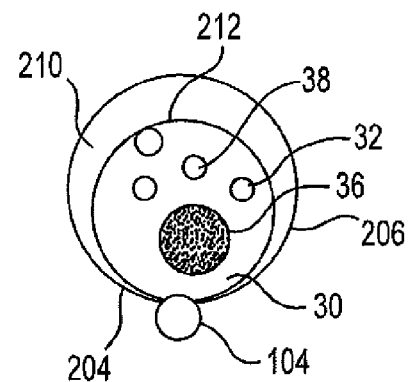
Fig. 3
Fig. 4

NEEDLELESS INJECTION DEVICE COMPONENTS, SYSTEMS, AND METHODS

PRIORITY CLAIM

The present patent application is a continuation-in-part (CIP) of International Application Number PCT/US2009/006384, filed Dec. 4, 2009, which in turn claims priority under 35 USC §119(e) to provisional application Ser. No. 61/139,974, filed Dec. 22, 2008, by Crank, entitled ELASTIC ADAPTER FOR FLEXIBLE SCOPE COMPATIBLE INJECTION DEVICE; provisional application Ser. No. 61/122,808, filed Dec. 16, 2008, by Crank, entitled TWO-PIECE SIDE-FIRING JET INJECTION CATHETER; and provisional application Ser. No. 61/122,793, filed Dec. 16, 2008, by Crank, entitled URINARY TRACT CATHETER WITH SHAPEABLE TIP. The present patent application also claims priority to provisional application Ser. No. 61/226,864, filed Jul. 20, 2009, by Rykhus, Jr., entitled HIGH-PRESSURE INJECTION SYSTEM HAVING DIRECTIONAL APPOSITION DEVICE; provisional application Ser. No. 61/226,840, filed Jul. 20, 2009, by Ogdahl, entitled INJECTION CATHETER AND OPTICAL DEVICE MOUNTING SYSTEM; and provisional application Ser. No. 61/226,844, filed Jul. 20, 2009, by Rykhus, Jr., entitled MULTI-CHANNEL HIGH-PRESSURE INJECTION SYSTEM AND METHOD, each of these applications being incorporated herein by reference in their entireties.

FIELD OF THE INVENTION

The present invention relates generally to jet injection devices for the delivery of therapeutic fluids to a treatment site. Described device and method embodiments involve a fitting such as an elastic adapter or other removable or permanent fitting to attach to a distal end of a shaft. Exemplary elastic adapters can be elastically stretched to fit over a distal end of a flexible scope or other medical device shaft. Other exemplary adapters can involve non-elastic mechanisms. Optionally and preferably an injection shaft such as a non-metal reinforced polymeric injection tube can be mounted to the fitting (e.g., elastic adapter) so as to be aligned parallel to the flexible scope. In other embodiments, an adapter can be attached to an injection shaft that is movably disposed within a lumen of a flexible scope or other medical device shaft.

BACKGROUND

Lower urinary tract health is an increasingly important health issue, e.g., based on an aging population. Treatment of lower urinary tract conditions is an area of much investigation. Prostate disease, for example, is a significant health risk for males. Diseases of the prostate include prostatitis, benign prostatic hyperplasia (BPH, also known as benign prostatic hypertrophy), and prostatic carcinoma.

Prostatitis is an inflammation of the prostate gland. Types include acute and chronic bacterial forms of prostatitis, and a non-bacterial form. Symptoms can include difficult urination, burning or painful urination, perineal or lower back pain, joint or muscle pain, tender or swollen prostate, blood in the urine, or painful ejaculation. Prostatitis is caused by bacterial infection in many instances, in which case treatment generally includes antimicrobial medication. Noninfectious forms of prostatitis are treated by other means such as administration of an alpha-1-adrenoreceptor antagonist drug to relax the muscle tissue in the prostate and reduce the difficulty in urination.

Benign prostatic hypertrophy (BPH) is a very common disorder affecting an estimated 12 million men in the United States alone. BPH is a chronic condition and is strongly age-related; approximately 50% of men over the age of fifty, 75% of men beyond the age of seventy, and 90% of men over the age of eighty are afflicted with BPH. BPH is a non-cancerous condition characterized by enlargement of the prostate, obstruction of the urethra, and gradual loss of bladder function. Symptoms include difficult urination, frequent urination, incomplete emptying of the bladder, and urgency.

BPH may be treated with a number of therapeutic modalities including surgical and medical methods, depending on severity of symptoms. Treatments range from "watchful waiting" for men with mild symptoms, to medications, to surgical procedures. Examples of useful medications include 5-alpha reductase inhibitors such as Avodart™ and Proscar®.

Transurethral resection of the prostate (TURP) is a preferred surgical method of treating BPH. A typical TURP procedure requires general anesthesia and the placement of a resectoscope in the urethra for removal of multiple small chips of hyperplastic prostatic tissue to relieve the obstruction. Complications from TURP include bleeding, incontinence, retrograde ejaculation, and impotence.

An alternate surgical method for treating BPH is transurethral incision of the prostate (TUIP). In the TUIP procedure, incisions are made in the prostate to relieve pressure and improve flow rate. Incisions are made where the prostate meets the bladder. No tissue is removed in the TUIP procedure. Cutting muscle in this area relaxes the opening to the bladder, which decreases resistance to urine flow from the bladder. A variant of the TUIP procedure in which a laser is used to make the incision is known as transurethral laser incision of the prostate (TULIP).

Other surgical methods used to relieve the symptoms of BPH include methods of promoting necrosis of tissue that blocks the urethra. Hyperthermic methods, for example, use the application of heat to "cook" tissue and kill the cells. The necrosed tissue is gradually absorbed by the body. Several methods of applying heat or causing necrosis have been demonstrated, including direct heat (transurethral needle ablation, or TUNA), microwave (transurethral microwave treatment, or TUMT), ultrasound (high-intensity focused ultrasound, or HIFU), electrical vaporization (transurethral electrical vaporization of the prostate, or TUEVP) and laser ablation (visual laser ablation of the prostate, or VLAP), among others.

Chemical ablation (chemoablation) techniques for promoting prostate tissue necrosis have also been considered. In one chemical ablation technique, absolute ethanol is injected transurethrally into the prostate tissue. This technique is known as transurethral ethanol ablation of the prostate (TEAP). The injected ethanol causes cells of the prostate to burst, killing the cells. The prostate shrinks as the necrosed cells are absorbed.

In addition to prostate conditions, other tissue of the urinary tract can be affected by medical conditions that can be treated by delivery of various therapeutic materials in the form of fluids. Tissues of the bladder (which includes the bladder neck), ureter, kidneys, urethra, as well as the prostate, can be treated by delivery of drugs or other therapeutic agents, such as botox. Therapeutic agents should be delivered with minimized discomfort and procedure time, and with the best degree of accuracy of delivery location and delivery volume as possible. As such, there exists continuing need to provide improved devices for delivering therapeutic fluids to the lower urinary tract, kidneys, ureters, etc. A wide variety of medical treatments are at least partially performed through the delivery and introduction of therapeutic compositions to a treatment location. In home or outpatient settings, typical delivery methods can comprise oral delivery, via liquid or solid forms, as well as a variety of inhalant style devices. In clinical or hospital settings, therapeutic fluids can be injected using needle based or in some minimally invasive procedures. The therapeutic fluid can be delivered through a tubular device such as a catheter or endoscope based systems.

One way in which therapeutic fluids can be delivered internally is through the use a tube-like device configured to provide a jet-injection of the therapeutic fluid at a desired treatment site. Generally, a remote injector is utilized to deliver the therapeutic fluid from an external reservoir located at a proximal end of the tube-like device so such administration can occur at a distal end of the tube-like device. Due to the relatively long travel length of the therapeutic fluid through the tube-like device, the remote injector must generally be capable of pressurizing the therapeutic fluid to pressures exceeding about 200 pounds per square inch, e.g., a pressure of 2,000 psi. In order to accommodate these pressures, the tube-like devices have been fabricated of alloys such as NiTi or stainless steel or with metal-reinforced polymers such as the braided tubes typically found in catheters.

Currently a number of manufacturers make a variety of flexible scopes to navigate the tortuous paths often found in the human body. Scopes such as cytoscopes, endoscopes, ureteroscopes, choledoscopes, and hysteroscopes vary slightly in size and shape by brand. There is advantage to using existing scopes for directing an injection device to a treatment site. Furthermore, there is advantage to controlling the overall size of the injection system and scope so as minimize the invasiveness of the procedure.

SUMMARY

The invention relates generally to needleless or high-pressure injection devices useful for injecting fluid to tissue, such as tissue of the lower urinary tract including the prostate or bladder. The devices inject a therapeutic fluid or "injectate" at high-pressure using an orifice at the end of an elongate shaft inserted into a body lumen such as the urethra. To treat the prostate, injectate fluid can be passed through the urethra and dispersed in the prostate as a cloud of particles. Devices of the present description can be useful to treat tissue of the urinary tract in females or males. For example, devices as described may be useful to inject the bladder, bladder neck, the urethral tissue itself or the external sphincter, or for transurethral injection of the prostate in a male. In other embodiments, a fluid may be injected into tissue of the urinary tract (e.g., bladder, urethra, kidneys, ureters, prostate, etc.) such as individual or combination treatments using drugs or other therapeutic agents, e.g., botulism toxin ("botox"), an antiandrogen, among others as will be understood.

The needleless systems can overcome undesired or disadvantageous features of systems and methods that use a needle, e.g., for transurethral injections of fluid into the prostate or the bladder. A needleless mode of injecting a fluid into the prostate or other tissue of the lower urinary tract requires that certain technical challenges be overcome to accommodate the specific technical and medical needs of injecting a therapeutic fluid to internal tissue, optionally transurethrally, without a needle. For instance, to inject the prostate, a needleless injector must be of a size and shape that may be placed within the urethra while also providing an injectate at the injection orifice in the prostatic urethra at a pressure sufficient to penetrate urethral and prostate tissues. The injectate must penetrate urethral and prostate tissues in a predictable and desired fashion to become dispersed throughout the tissue.

Features of described needleless injector devices are included as part of the present disclosure and may be included in a needleless injector device individually or in any desired combination. For example, embodiments of the invention include needleless injector devices that include positioning features that facilitate proper positioning of an injection orifice in the urethra. Positioning features are various in nature and may include one or more of: a balloon or multiple balloons located at the distal end of the device for placement and fixing the distal end; multiple orifices; moveable orifices; demarcation of distances to distal end features, at the proximal end; and an optical feature such as an endoscope or optical fiber. Other embodiments of needleless injector devices include the above features along with one or more tissue tensioners that contact and optionally place pressure on tissue at a desired location relative to an injection orifice, and optionally can also place a strain or tension on the tissue as desired for delivery of an injection at the surface of the tissue. Examples of tissue tensioners include inflatable or extendable features such as balloons or mechanically extendable features such as paddles, metal cages, other mechanically extendable protrusions, vacuum, etc.

Needleless injector devices as described can be used with various delivery methods such as methods that allow for direct vision of an injection wherein an internal location of an injection orifice is determined visually, and methods referred to as blind delivery methods wherein location of an injection orifice is determined indirectly. Direct vision methods can involve the use of an optical feature to view an injection site directly, such as by use of an endoscope or optical fiber that is included in an injector device, e.g., as a component of the shaft. A device that allows for blind delivery can instead include one or more non-optical features that allow a surgeon to identify the position of a device, and in particular an injection orifice, e.g., within the urethra, so that an injection can be performed at a desired location. Blind delivery techniques can identify a delivery location based on features of the device such as a length-measuring feature such as demarcations at the proximal end of the device that reference locations and provide visualization of features at the distal end, by using demarcations in combination with known dimensions of a device and of anatomy. Demarcations may be used also in combination with measurement of anatomical features such as the length of the prostate, e.g., by known techniques including those that use ultrasound or x-ray position measuring equipment. Blind delivery techniques can also involve other features of devices as described herein such as positioning features (e.g., balloons at the distal end of the device) and moveable injection orifices.

Devices described herein allow for localized delivery of therapeutic fluids that include biologically active species and agents such as chemical and biochemical agents at desired anatomical tissue locations, e.g., at tissue of or near a body lumen, including but not limited to locations in the male or female urinary tract, e.g., urethra, prostate, bladder, bladder neck, etc. Exemplary devices can be designed to deliver fluid at various tissue locations, optionally also multiple different therapeutic fluids or multiple different tissue locations.

Embodiments of exemplary devices include a tissue tensioner attached (removably or otherwise, such as through a removable or non-removable fitting) to a distal end of a shaft, which may be a working shaft or an injection shaft.

Other embodiments of exemplary devices include a fitting at a distal end of a shaft, e.g., a removable fitting or a non-removable fitting, to attach one distal end structure to another distal end structure. A fitting may be used, for example, to attach one distal end of a shaft (such as an injection shaft distal end) to another distal end of a shaft (such as a working shaft distal end). A distal end of a shaft may also optionally attach or be attached to a tissue tensioner optionally through the fitting or otherwise; the optional tissue tensioner may be associated with (e.g., integrally connected to or removably attached to) the fitting, or may be associated with the injection shaft or the working shaft apart from the fitting.

Still other exemplary embodiments include a tissue tensioner and a fitting in the form of a tissue tensioner assembly. The fitting may be a fitting that attaches to a distal end of a shaft (e.g., working shaft or injection shaft), removably or non-removably.

In slightly more detail, certain exemplary devices include a tissue tensioner assembly comprising a tissue tensioner and a fitting, wherein the fitting can be attached to a distal end of a shaft. The fitting can be attached to a shaft, such as an injection shaft or a working shaft, in a removable or a non-removable, e.g., semi-permanent or permanent, fashion. As used herein, a fitting is considered "removable" if the fitting can be attached to a shaft in a manner sufficiently secure to allow the fitting to remain securely attached to the shaft during an injection procedure without the fitting becoming undone, and the fitting can be removed from the shaft without permanently damaging the shaft or the fitting so at least one of the fitting or the shaft can be re-used.

In certain embodiments a tissue tensioner (e.g., as part of a tissue tensioner assembly) can be attached (removably or non-removably) to a distal end of an injection shaft, and the injection shaft can be inserted into a working lumen of a working shaft. Optionally a proximal end of the injection shaft can be inserted into a distal end of the working lumen (alternately a distal end of the injection shaft can be inserted into a proximal end of the working lumen) and the injection shaft can be placed within the length of the working lumen. A tissue tensioner assembly can be attached to the distal end of the injection shaft, before or after inserting the injection shaft into the working shaft. The tissue tensioner assembly may include an elongate actuating shaft, lumen, or mechanism that extends to a proximal end; a proximal end of this elongate shaft, lumen, or actuating mechanism can also be inserted into a distal end of the working lumen.

In alternate embodiment a tissue tensioner (e.g., in the form of a tissue tensioner assembly) can be attached to a distal end of a working shaft, such as by use of a fitting and in a removable or non-removable fashion. An injection shaft can be associated with the working shaft; for example an injection shaft can be secured adjacent to the working shaft, lengthwise along an external surface of the working shaft, optionally by attachment to the same fitting that attaches to the working shaft and to the tissue tensioner. Alternately an injection shaft may be placed permanently, removably, integrally, securely, or movably, within a working shaft, such as but not necessarily within a working lumen.

Exemplary embodiments of described devices can include a non-metal, polymeric tube-like device (e.g., an "injection lumen") for delivering a therapeutic fluid to a treatment site within a patient, attached (removably or non-removably) at a distal end to an elastic adapter (or other type of removable "fitting," included but not limited to elastic adapters) sized to fit over a flexible scope (or "working shaft") distal end. An exemplary fitting can be an elastic adapter in the form of a sleeve-like device disposed about a distal end of the flexible scope. The exemplary elastic adapter may be manufactured from compliant or semi-compliant material. The elastic adapter has a diameter less than the outer diameter of the scope associated with the injection treatment. The needle-less injection lumen (or "injection shaft") may be attached to the outer diameter of the elastic adapter or to an inner diameter with the injection port (or "injection orifice") disposed adjacent to an aperture (in the adapter). The elastic adapter may also include an upper rim to prevent the elastic adapter from axially sliding from the distal end of the scope.

In one embodiment, an elastic adapter may be a two layer device so as to include an inflation element (or "inflatable balloon" that can function as a "tissue tensioner"). An inner elastic sleeve comprises a first layer. The first layer is elastically mounted about the distal end of a flexible scope (e.g., working shaft). As the flexible scope is stiffer than the elastic adapter, the elastic tension created by the stretched elastic adapter does not impinge upon the scope. The second layer is attached around the outer diameter of the first layer to create a balloon. A balloon inflation lumen is disposed axially along a central aperture (of the working shaft) with a first end in communication with a media source such as compressed air or a fluid. A second end of the balloon inflation lumen is in communication with the space between the first and second layer. It is envisioned that the second layer may radially overlap the axial ends of the first layer. In this embodiment, the injection lumen may be attached to the second layer.

It is further envisioned that in some embodiments the second layer may only partially surround the first layer. For example, the second layer maybe disposed eccentrically around the first layer leaving an axial section of the first layer exposed. The injection lumen would thus be attached to the first layer along the exposed section. As the apposition balloon inflates the injection lumen can thus be positioned. The eccentric geometry allows the apposition balloon to force the injection lumen against the tissue chosen for treatment.

A non-metal, polymeric tube-like injection device (e.g., injection shaft) can be fabricated using suitable high strength polymers including, for example, polyimide, polyetherimide available from General Electric under the trade name Ultem® and linear aromatic polymers such as PEEK™ available from Victrex plc. In some embodiments, a non-metal, polymeric tube-like device can be reinforced through the inclusion of materials including nano-particles, clays and/or glass. In some presently contemplated embodiments, the non-metal, polymeric tube-like device can be reinforced with one or more polymers such as, for example, tubes braided with Kevlar or other high-strength polymers. The non-metal, polymeric tube-like device can be fabricated so as to have a burst strength exceeding at least about 200 pounds per square inch, e.g., exceeding 1,000 or 2,000 psi, and in some embodiments, having a burst strength within a range of about 2,000 psi to about 5,000 psi. The non-metal, polymeric tube-like device can be fabricated so as to have distention properties, wherein an orifice or jet port located at a distal end of the polymeric tube-like device retains its shape and/or size without suffering swelling that can have a detrimental impact on a fluid jet used to deliver the therapeutic fluid at the treatment site.

In one aspect the invention relates to a tissue tensioner assembly capable of being connected to an elongate shaft. The tissue tensioner assembly includes: a tissue tensioner comprising an expandable surface capable of exhibiting an expanded state and a non-expanded state, and a fitting connected to the tissue tensioner, the fitting capable of attaching the tissue tensioner to a shaft.

In another aspect the invention relates to an elongate shaft capable of injecting fluid into tissue. The shaft includes: a working shaft comprising a working shaft proximal end, a working shaft distal end, and a working lumen extending between the working shaft proximal end and the working shaft distal end; an injection shaft comprising an injection shaft proximal end and an injection shaft distal end, the injection shaft moveably disposed within the working lumen; and a tissue tensioner located at the injection shaft distal end, the tissue tensioner comprising an expandable surface capable of exhibiting an expanded state and a non-expanded state.

In yet another aspect the invention relates to an elongate shaft capable of injecting fluid into tissue. The shaft includes: a working shaft comprising a working shaft proximal end and a working shaft distal end, and an injection shaft comprising an injection shaft proximal end and an injection shaft distal end. The injection shaft distal end is attached to the working shaft distal end by a removable fitting.

In yet another aspect the invention relates to a method of connecting a working shaft distal end and an injection shaft distal end. The method includes: providing a fitting assembly comprising an injection shaft distal end and a removable fitting capable of being attached to a working shaft distal end, and attaching the removable fitting to the working shaft distal end.

In yet another aspect the invention relates to a method of assembling a shaft and tissue tensioner. The method includes: providing a tissue tensioner assembly comprising a tissue tensioner comprising an expandable surface capable of exhibiting an expanded state and a non-expanded state, and a fitting connected to the tissue tensioner; and attaching the fitting to an elongate shaft.

In another aspect the invention relates to a method of assembling a shaft and tissue tensioner. The method includes: providing an injection shaft comprising an injection shaft proximal end, an injection shaft distal end, and a tissue tensioner at the injection shaft distal end, the tissue tensioner comprising an expandable surface capable of exhibiting an expanded state and a non-expanded state; providing a working shaft comprising a working shaft distal end, a working shaft proximal end, and a working lumen extending between the working shaft distal end and the working shaft proximal end; and inserting the injection shaft proximal end into a distal end of the working lumen.

In another aspect the invention relates to a combination of two or more components of a needleless injection system selected from: a console, a removable pressure chamber, an injection shaft, a tissue tensioner, a fitting, and a working shaft.

In yet another aspect the invention relates to tissue tensioner assembly comprising a tissue tensioner, a fitting, and an adapter. The tissue tensioner includes an inflatable balloon, the fitting is connected to the tissue tensioner and is capable of attaching to a shaft, and the adapter is capable of connecting to a lumen assembly that includes an inflation lumen and an injection lumen. The adapter is in fluid communication with an interior of the expandable balloon.

In another aspect the invention relates to a needleless injection device capable of injecting fluid into tissue. The device includes: a working shaft comprising a working shaft proximal end and a working shaft distal end; a lumen assembly comprising a proximal end, a distal end, a tubular inner shaft extending from the proximal end to the distal end, and a tubular outer shaft extending from the proximal end to the distal end, an injection lumen being located at an interior of the tubular inner shaft, and an inflation lumen being located at an annular space between the tubular inner shaft and the tubular outer shaft, and a tissue tensioner engaged with the working shaft, the tissue tensioner comprising an inflatable balloon in fluid communication with the proximal end of the inflation lumen.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 3 is an alternate two layer embodiment of an elastic adapter with a therapeutic fluid delivery system for delivering a therapeutic fluid disposed about a flexible scope according to the present disclosure.

FIG. 4 is a sectional view of the alternate embodiment of FIG. 3.

Figure 1:
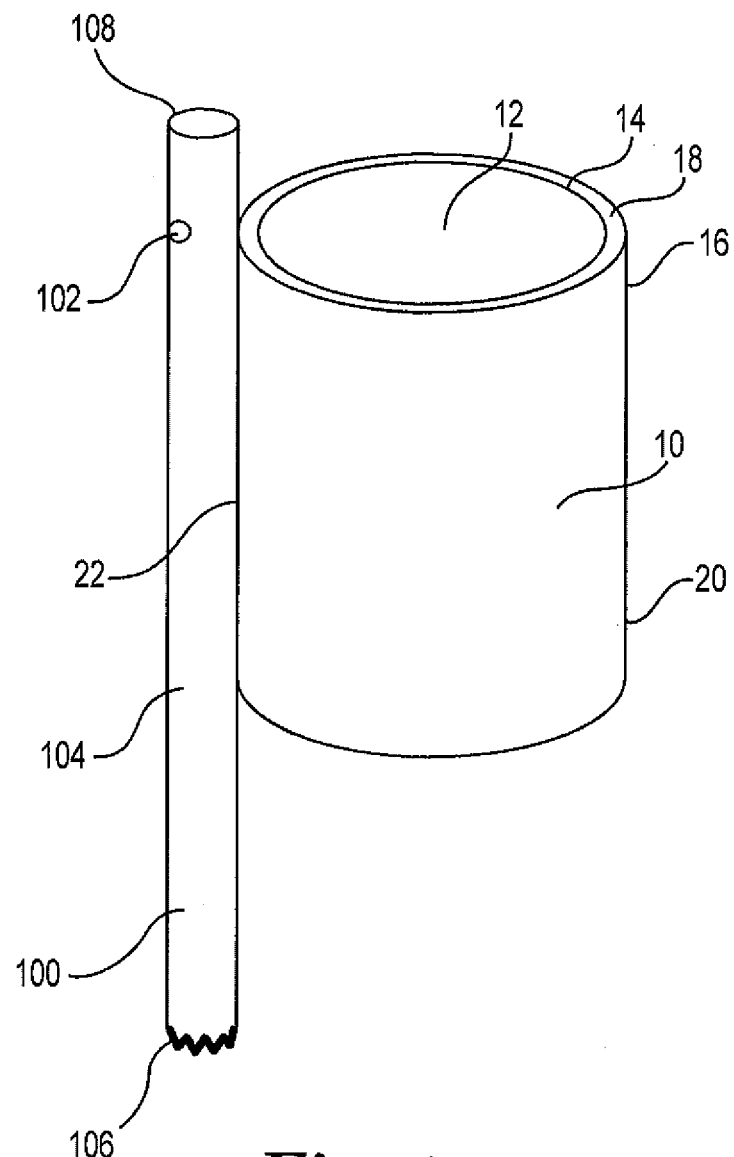
FIG. 1 is a perspective view of an embodiment of an elastic adapter (fitting) with a therapeutic fluid delivery system for delivering a therapeutic fluid to a treatment location according to the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION

In the following detailed description of the present invention, numerous specific details are set forth in order to provide a thorough understanding of the present invention. However, it will be obvious to one skilled in the art that the present invention may be practiced without these specific details. In other instances, well-known methods, procedures, and components have not been described in detail so as to not unnecessarily obscure aspects of the present invention.

The invention relates to devices comprising a shaft for injecting a fluid into tissue, such as a needleless injection device. Needleless devices as described generally include a distal end and a proximal end. As used herein, the "distal end" refers to a portion of the device that is located internally within a patient's body during a treatment procedure, generally including the distal end of an elongate shaft; i.e., a distal end or distal portion of a device or a component is the end or portion that is toward the patient, and the "proximal" end or portion of the device or component is the end or portion toward the surgeon or operator of the device.

A shaft distal end may include functional features that operate on fluid or tissue during use, such as one or more injection orifice, optional delivery head (end effector, nozzle, etc.) to house one or more injection orifices, optionally a tissue tensioner (as described), optionally a fitting to attach one component of a shaft distal end to one or more other component, optionally one or more of a light, optical feature, steering feature, etc. A "proximal end" of an exemplary needleless device can include an injector body or "console" that remains external to the patient during use. An exemplary console can include a housing that connects to or is otherwise (directly or indirectly) in fluid communication with the shaft. The console can include fluid that can be pressurized by a pressure source to cause the fluid to flow through the shaft for injection into tissue at the distal end. The term "distal end tip" refers to a terminus of a distal end; for example, a distal end tip of a shaft is the location that defines the shaft end itself, as opposed to a portion of a length of a shaft that is referred to as a "distal end."

A device can eject fluid from at least one injection orifice located at the distal end of the shaft. Optionally, multiple injection orifices may be located at one or more locations along a length of or about a circumference of a shaft distal end. Devices, systems, and methods as described can be used to inject fluid (sometimes referred to as an "injectate" or "injection fluid," which may be any type of fluid such as a therapeutic fluid) into tissue in a needleless manner whereby the injectate passes as a pressurized fluid stream (or "jet") through a surface of a tissue, penetrating without the use of a needle through the tissue surface and into the bulk of the tissue, and dispersing as particles or droplets within the tissue below the tissue surface. This contrasts with injections performed using a needle, whereby a hollow needle structure is used to penetrate tissue to locate a hollow end of the needle within a tissue mass, below the tissue surface, after which the needle carries fluid into the bulk of the tissue and delivers the fluid at a relatively low pressure to the tissue in the form of a body or pool of fluid known as a bolus.

A fluid stream or jet ejected for injection into tissue by a needleless injection system can be of a size (e.g., diameter), velocity, pressure, and volume to allow the fluid stream to penetrate directly through a tissue surface, then disperse within the tissue. The stream can be considered to be a relatively high velocity, high pressure, small diameter jet that after entry through a tissue surface disperses within the tissue, preferably as a multi-directional collection of particles (e.g., a "cloud") or droplets within the bulk of the tissue. Exemplary pressures of a fluid at a pressure chamber can be at least 200 pounds per square inch (psi), e.g., from 300 to 5000 pounds per square inch. Without limiting the scope of the present description: when injecting bladder tissue a pressure of from 250 to 1000 psi can be effective, measured at the pressure chamber; when injecting prostate tissue a pressure of from 3500 to 5000 psi can be effective, measured at the pressure chamber.

Exemplary needleless devices may be used for treating various physical ailments or conditions at any bodily tissue, for example to treat tissue that contains or is within reach of injection through a body cavity or body lumen, e.g., by accessing tissue through a body lumen, vessel, or cavity, and injecting tissue by placing an injection orifice within the lumen, vessel, or cavity. The type of tissue injected for treatment can be any amenable tissue, especially tissue accessible through a body lumen such as prostate tissue accessible through a urethra.

Exemplary needleless fluid delivery devices or systems can include a proximal end that includes a console, and an elongate shaft extending from a proximal end in communication with the console to a distal end. The elongate shaft can include an injection shaft and an injection lumen, optionally disposed permanently, semi-permanently, or loosely and movably within or adjacent to a working lumen. A distal end of the injection shaft can include one or more injection orifice in fluid communication with the console, through an injection lumen.

A console generally can include a housing, a pressure chamber, and a pressure source. A console can be of any configuration, size, or design, ranging from a small, handheld design to a relatively larger floor or table-mounted console. Optionally a console can include separate or separable components such as a pressure chamber (e.g. "connector member") that can be attached between a housing and a proximal shaft end, used for an injection procedure, and detached and optionally discarded. A shaft (e.g., an injection shaft or a working shaft, or a shaft assembly containing one or more of an injection shaft or an inflation shaft) can also be attached to a console, pressure chamber, or connector member, in a manner to allow separation and optional re-attachment or disposal after one or more use. With separable components, a shaft or pressure chamber can be attached to a console housing and used to inject a first patient or a first injectate; the shaft or pressure chamber (e.g. "connector member") can then be discarded or sterilized. A second shaft or pressure chamber can be attached to the console to treat a second patient or the first patient with second injectate or another amount of the first injectate. The second patient or injectate can involve injection and treatment of the same type of tissue as the first patient or injectate, or of a new type of tissue (e.g., prostate or bladder). In this manner, separable and optionally disposable shaft or pressure chamber components of a needleless injection system can allow a console housing to be used multiple times to inject the same or different injectates, to the same or different patients, and to the same or different types of body tissue.

A console can include actuating features to control distal end features, e.g., for steering a steerable distal end of a steerable shaft, to actuate ejection of fluid, to move a moveable or extendable injection shaft or one or more injection orifice relative to another shaft component such as a working shaft, optional ports to connect a console housing to auxiliary devices, electronics such as controls, optic features such as a lens, fiber optic, or electronic viewing mechanism to allow viewing through an optical feature (to view a location of delivery), and an actuating mechanism or pressure source for a tissue tensioner in the form of a mechanical tissue tensioner or an inflatable balloon. One or more attachment ports can optionally attach a console to an external and optionally remote component such as an external or remote pressure source, vacuum source, or an external or remote fluid reservoir to supply injectate or other fluid, such as to inflate a balloon. For example, a console (e.g., console housing or connector member) may have a fluid port that attaches to a source of a fluid to supply the fluid to the console, such as to a permanent or detachable pressure chamber. Embodiments of consoles can include a permanent or removable pressure chamber and a pressure source capable of pressurizing a fluid contained in the pressure chamber to cause the fluid to flow from the console, through a lumen in the shaft, and then through an injection orifice.

A fluid chamber can be a space (volume) at a proximal end of a device such as at a console housing, useful to contain pressurized or non-pressurized fluid, such as injectate or a gaseous or liquid fluid to inflate a balloon (e.g., tissue tensioner). Examples of specific types of fluid chambers include fluid reservoirs and pressure chambers. Optionally a proximal end of a device may include one or multiple fluid reservoirs and pressure chambers.

A fluid reservoir is generally a type of fluid chamber that can contain a fluid for a purpose of containing, transferring, holding, or storing a fluid, such as a fixed volume fluid chamber, and may be included as a permanent or removable (attachable and detachable) component of a console.

A pressure chamber can be a type of fluid chamber for containing fluid (e.g., injectate) for a purpose of placing the fluid under pressure to deliver the fluid through a lumen to a distal end of a shaft for ejection from an ejection orifice. Examples of pressure chambers include a syringe chamber and other variable volume spaces that can be used to contain and pressurize a fluid. Examples of variable volume pressure chambers include spaces that can exhibit a variable volume based, e.g., on a plunger, piston, bellows, or other mechanism for increasing or decreasing the volume (and correspondingly decreasing or increasing pressure) within the variable volume chamber space. A pressure chamber can be pressurized by a pressure source attached to the plunger, bellows, or piston, etc., such that fluid contained in the pressure chamber is ejected under pressure, e.g., for priming a device, or for ejecting fluid from an ejection orifice for injection or to produce a control force. A pressure source may be any source of energy (e.g., mechanical, electrical, hydraulically derived, pneumatically derived, etc.) such as a spring, solenoid, compressed air, manual syringe, electric power, hydraulic, pneumatic pressure sources, etc. A pressure chamber may be a permanent or removable (attachable and detachable) component of a console.

Examples of consoles, console features and combinations of console features that can be useful according to the present description are identified at U.S. Pat. Publ. Nos. 2006-0129125 and 2009-0312696, and in Assignee's copending patent applications PCT/US2009/006383, filed Dec. 4, 2009, entitled METHOD AND APPARATUS FOR COMPENSATING FOR INJECTION MEDIA VISCOSITY IN A PRESSURIZED DRUG INJECTION SYSTEM, by Crank; WO 2010/065126 A2; WO 2010/065127 A2; entitled NEEDLELESS INJECTION DEVICE COMPONENTS, SYSTEMS, AND METHODS filed on even date herewith; AMS0181/WO entitled DEVICES, SYSTEMS, AND RELATED METHODS FOR DELIVERY OF FLUID TO TISSUE filed on even date herewith; AMS0182/WO entitled DEVICES, SYSTEMS, AND METHODS FOR DELIVERING FLUID TO TISSUE filed on even date herewith; AMS0183/WO entitled HIGH PRESSURE INJECTION CATHETER SYSTEMS filed on even date herewith; and AMS0184/WO entitled NEEDLELESS INJECTION DEVICE COMPONENTS, SYSTEMS, AND METHODS filed on even date herewith, the entireties of these documents being incorporated herein by reference.

In communication with a proximal end of a device is an elongate shaft that extends from the proximal end (i.e., from a proximal shaft end), that is optionally removably connected to the console (or a component of the console such as a removable pressure chamber), to a distal end that can be placed in a patient during an injection procedure. A shaft can be of various designs, minimally including an injection lumen to carry injectate from a proximal end of the device to a distal end of the injection shaft. Shafts for needleless devices as described are also described in Assignee's copending patent application WO 2010/065133 A2.

An injection shaft minimally includes an injection lumen in communication with an injection orifice. The injection shaft can include structure such as sidewalls that define the injection lumen, the sidewalls being of sufficient strength to withstand operating pressures sufficient to deliver injectate from the injection orifice at an elevated pressure sufficient to cause the injectate to be ejected from the injection orifice to penetrate a tissue surface and become injected and into and dispersed below the tissue surface, as described herein. Exemplary elevated pressures ("injection pressures") may be at least 200, e.g. 1,000, or 2,000 pounds per square inch or greater as measured at the distal end of the injection lumen, or at the pressure chamber. An injection shaft may be of a flexible material (e.g., a metal or polymeric tube) that can withstand such injection pressure, and may be prepared from exemplary materials capable of withstanding pressure of an injection, e.g., nitinol, stainless steel, reinforced (e.g., braided) polymer, as also described elsewhere herein.

A basic version of a useful shaft as described can be an "injection shaft" that includes a proximal end, a distal end, a sidewall that defines an internal lumen ("injection lumen"), and at least one injection orifice at the distal end in connection with the injection lumen.

An injection shaft can be any elongate structure capable of delivering fluid to a distal end of the injection shaft at a pressure suitable to inject tissue, as described. Exemplary injection shaft structures include relatively flexible hollow bodies having a distal end, a proximal end, sidewalls extending between the ends, an internal lumen defined by interior surfaces of the sidewall. The injection lumen is in communication with one or more injection orifice at the distal end; the injection orifice may be as described herein, such as an aperture or bore in an injection shaft sidewall, an aperture or bore in a nozzle, end effector, injection head, or other structure in communication with the injection lumen.

An exemplary injection shaft can be in the form of a non-metal, polymeric tube-like device and can be fabricated using suitable high strength polymers including, for example, polyimide, polyetherimide available from General Electric under the trade name Ultem® and linear aromatic polymers such as PEEK™ available from Victrex plc for transporting the treatment fluid to the treatment area. In some embodiments, the non-metal, polymeric tube-like device can be reinforced through the inclusion of materials including nano-particles, clays and/or glass. In some presently contemplated embodiments, the non-metal, polymeric tube-like device can be reinforced with one or more polymers such as, for example, tubes braided with Kevlar or other high-strength polymers. The non-metal, polymeric tube-like device can be fabricated so as to have a burst strength exceeding at least about 200, e.g., 1,000 or 2,000 psi and in some embodiments, having a burst strength within a range of about 2,000 psi to about 5,000 psi. The non-metal, polymeric tube-like device can be fabricated so as to have distention properties, wherein one or more orifices or jet ports located at a distal end of the polymeric tube-like device retains its shape and/or size without suffering swelling that can have a detrimental impact on a fluid jet used to deliver the therapeutic fluid at the treatment site. See, e.g., U.S. Pat. Publ. No. 2008/0119823.

An exemplary injection shaft can include a sidewall that defines an outer shaft surface and an inner injector lumen, these being of continuous and relatively uniform dimensions of inner diameter, outer diameter, and wall thickness, along an entire length of the injection shaft. Alternately, an injection shaft, injector lumen, or sidewall, may change dimensions (e.g., wall thickness) along the length of the injection shaft, with a larger wall thickness (e.g., greater outer diameter) at a proximal end and a thinner wall thickness (e.g., reduced outer diameter) at the distal end. An example of an inner diameter of an injection shaft (i.e., a diameter of an injection lumen) can be greater than 0.020 inches, e.g., from 0.022 to 0.030 inches (for a lumen made of polyetheretherketone, or "PEEK"); exemplary outer diameters for the same exemplary injection shaft may be at least 0.032 inches e.g., from 0.034 to 0.045 inches. (An inner dimension of a fitting for placement on such an injection shaft may be, e.g., in the range from about 0.03 to about 0.05 inches.) A length of an injection shaft can be any length that functions to place a proximal end at a console and a distal end at a desired tissue location; exemplary lengths can be from as little as 15 inches if the console is a hand-held console, to as long as 100 inches if the console is floor based or table based.

An injection shaft can be a component of a shaft of a useful needleless injection device or system. Other shaft components may include additional elongate shaft structures with desired functionality, a single example being a device referred to herein as "medical device shaft" or a "working shaft," which can be used to securely or moveably support or house an injection shaft. For instance, an injection shaft can be incorporated permanently or movably (e.g., removably) against (alongside) or within (e.g., in a "working lumen" of) a working shaft. In exemplary embodiments an injection shaft can be loosely contained in a working lumen of a working shaft to allow movement of the injection shaft length-wise and rotationally relative to the working shaft; an injection shaft may be capable of moving longitudinally within a working lumen to allow the injection lumen to be extended distally from an open end of a working lumen at a distal end of the working shaft.

An example of a "working shaft" or "medical device shaft" can be a shaft that is useful in conjunction with an injection shaft, to manipulate and place the injection orifice of an injection shaft at a desired location for treatment of tissue. A "working shaft" or "medical device shaft" can function to support the injection shaft and can optionally and preferably include any of a variety of optional functionalities such as steerability, an optical function, a tissue tensioner, or combinations of these, in addition to supporting the injection shaft.

An example of a particularly preferred working shaft can include features of a typical cystoscope, endoscope, ureteroscope, choledoscope, hysteroscope, catheter (e.g., urinary catheter), or the like, or other similar type of medical device shaft, including one or more feature of flexibility, an optical function, a steerable distal shaft end, and a working lumen. A working lumen can be sized to loosely house or contain the injection shaft, preferably in a manner to allow the injection shaft to be moved lengthwise and rotationally within the working lumen, relative to the working lumen, such as to allow the injection lumen (and optionally an attached tissue tensioner) to be extended from an opening at a distal end of the working lumen, at a distal end of the working shaft. A typical diameter (or other dimension) of a working lumen extending along a length of a distal end of a working shaft can be in the range from about 1 to about 3 millimeters. A typical length of working shaft for placement of a distal end at a location of the urinary tract can be, e.g., from 15 to 25 centimeters. A typical outside diameter of a working shaft may be, for example, from about 4 to about 10 millimeters.

As used herein, the term "flexible shaft" refers to a shaft (e.g., an injection shaft or a working shaft) that is sufficiently pliable to allow bending and flexing that allow the shaft to be inserted through the meatus or an external incision, into the urethra or another body lumen, and to allow a portion of a distal end of the shaft to be guided into a body lumen or body cavity such as a urethra and optionally the bladder neck or bladder, as can be done with a Foley catheter. A flexible shaft can be sufficiently soft and pliable to conform or partially conform to a patient's anatomy, such as would a Foley-type catheter. A "steerable" shaft is a type of a flexible shaft having a distal end that can be maneuvered directionally (e.g., bent or curved) from a proximal end; steerable shaft distal ends are sometimes features of endoscopes and other medical device shafts.

Optionally, a shaft of a device as described may also be malleable, or "shapeable," meaning that a shaft distal end, or portion thereof, can be of a material capable of being shaped to a form, and to remain in that form during use, such as for insertion into a body lumen, until re-formed. A shaft or a shaft component, such as a working shaft or an injection shaft, can include a malleable component such as a bendable metal wire, coil, ribbon, tube, or the like, capable of being shaped, used without substantial deformation, and re-shaped. A malleable distal end can allow a distal end to be shaped by a user to assist in placement of the distal end through a body lumen such as a urinary tract, at a desired location. In some methods of treatment, there may be difficulties or challenges in passing a shaft distal end through a body lumen, or to place the distal end in contact with tissue for injection. A malleable shaft distal end, e.g., of an injection shaft in particular, e.g., used in conjunction with a working shaft within which the malleable injection shaft distal end is moveably disposed, or in conjunction with a working shaft adjacent to which the malleable injection shaft distal end is disposed, may assist in overcoming such potential difficulties. The malleable distal end tip may be formed by a user to a desired curve or bend, before or after placement in a working channel or adjacent to a working shaft; the working shaft may be inserted into a body lumen such as a urethra, and the formed, malleable injection shaft distal end may be extended from or placed adjacent to the working shaft with a shape that improves the ability to position the injection shaft or an injection orifice thereof, at tissue for injection. A shapeable portion may vary in stiffness, length, resilience, material, radiopacity, etc., and may be of any malleable material such as a polymer, metal, or polymer-metal composite.

A distal end of an injection shaft includes one or multiple injection orifices for ejecting fluid within a body of a patient. An injection orifice can be any form of opening, aperture, or orifice, such as an aperture or bore in an injection shaft sidewall, or an aperture or bore in a nozzle, end effector, injection head, or other structure in communication with an injection lumen. Injection orifices can be located at relative locations and orientations along a length or circumference of an injection shaft distal end to result in ejection and distribution of ejected fluid in different directions (e.g., circumferentially relative to the shaft), optionally or alternately at different distances along the length of the injection shaft. An injection orifice can be directed at any angle relative to a longitudinal axis of a shaft, such as perpendicular, angled toward a distal end, or angled toward a proximal end.

An injection orifice may have any useful size (e.g., length and diameter) to produce a fluid stream of ejected fluid that can penetrate a tissue surface to become injected into tissue. Examples of a useful range of diameter of an injection orifice may be from about 0.001 to 0.05 inches, e.g., from 0.001 to 0.010 inches, depending on factors such as desired injection parameters (injection depth, volume, pressure, exit velocity, etc.) and the type and size (e.g., depth) of tissue being injected. An injection orifice may be larger or smaller than an injection lumen leading to the injection orifice, if desired, to affect the exit velocity of the jet of injectate from the injection orifice. Examples of useful orifice shapes may include features such as a venturi, a continuous uniform diameter along the length of an orifice, a funnel-shape, etc.

According to exemplary injection methods and devices, an injection orifice may be located on a proximal side of a distal end tip of an injection shaft, at a location that allows the injection orifice and adjacent injection shaft sidewall to contact a tissue surface as a longitudinal axis of a shaft that contains the injection orifice is positioned in an orientation that is parallel to the tissue surface. These device embodiments are sometimes referred to as "side-fire" devices, herein. As used herein, a "distal end tip" can be considered a location of a distal end of an injection shaft that is the farthest (most distal) feature of the injection shaft distal end.

In certain embodiments of "side-fire" devices an injection orifice can be located a distance away from a distal end tip on a proximal side of the distal end tip so the injection orifice is located to contact tissue for injection by placing the shaft sidewall in contact with tissue. Examples of injection orifice locations for these embodiments can be locations along a distal end of a shaft that are in the range from about 1 to about 40 millimeters from the distal end tip, on a proximal side of the distal end tip, e.g., such as a distance in the range from about 1 to about 25 millimeters from the distal end tip.

According to certain exemplary devices, a distal end of a shaft (injection shaft, working shaft, or the like) can include a tissue tensioner, the tissue tensioner optionally being attached to a shaft such as a working shaft, e.g., attached to the distal end of the shaft, by a fitting that is attached to the tissue tensioner, such as part of a tissue tensioner assembly. A tissue tensioner can be attached to or located at a distal end of a shaft, somewhat near to an injection orifice, e.g., to be within a body lumen such as a urethra, e.g., a prostatic urethra, and near the injection orifice when the distal end of the shaft is installed in a patient for injection. For example a tissue tensioner can be located at a length-wise location along an injection shaft, working shaft, or generally a shaft of a needleless injection device, that is the same length-wise location as the length-wise location of an injection orifice.

A tissue tensioner can comprise an expandable surface, e.g., a continuous expandable surface such as an inflatable balloon, or a non-continuous expandable surface such as an expandable metal (or plastic) cage or the like. The expandable surface can exhibit an expanded state and a non-expanded state. According to exemplary methods, a tissue tensioner can be placed in a body lumen in a non-expanded state and expanded within the lumen to the expanded state. In the expanded state, the tissue tensioner contacts an internal surface of the lumen to hold the distal end of the shaft and an associated injection orifice in place relative to desired tissue for injection. The tissue tensioner can optionally produce tension or strain on the tissue in a manner that can affect the manner in which an injected fluid stream penetrates the tissue surface and becomes distributed in the tissue upon injection. A tissue tensioner can facilitate a good result upon injection of fluid through luminal tissue by ensuring that the luminal tissue is fixed and includes a desired amount of tension for receiving an injection.

Depending on the configuration of an injection orifice at a shaft of a device, or at an injector head, a tissue tensioner can be used to place a desired portion of tissue in (e.g., direct) contact with an injection orifice, i.e., a surface that contains an injection orifice. Alternately, a tissue tensioner can place a desired portion of tissue at a desired distance away from an injection orifice, e.g., in the instance of an injector head that includes two surfaces with a recessed surface including an injection orifice. The distance, if any, between an injection orifice and tissue, at injection, can be selected to affect properties of the injection, e.g., to affect the distance an injectate penetrates into tissue, the size of droplets formed beneath the tissue surface, and the pattern over which droplets of injectate are dispersed throughout tissue when injected. Other factors can also be adjusted to affect properties of the injection such as pressure and volume of injectate, size and shape of the injection orifice, etc.

Examples of tissue tensioners include inflatable balloons located at a shaft distal end near an injection orifice (e.g., at the same length-wise location as the injection orifice), and mechanically extendable structures such as paddles, protrusions, levers, metal or plastic cages, metal or plastic springs or spirals, and the like, any of which can be include a surface that can be extended (e.g., mechanically) from a distal end of a working shaft or injection shaft to place pressure on internal tissue, e.g., on urethral tissue within the prostatic urethra or other luminal tissue. Tissue tensioners, device shafts, and related mechanisms and methods are described in Applicants' copending U.S. Patent Publ. Nos. 2006-0129125 and 2009-0312696, the entireties of both of these being incorporated herein by reference.

A balloon or a mechanically extendable tissue tensioner can be inflated or extended at a location that is approximately at a length along a distal end of a shaft that is near an injection orifice, e.g., at a length-wise location that is the same as the length-wise location of the injection orifice. When used within a lumen such as a urethra, the tissue tensioner can push luminal tissue (e.g., urethral tissue) away from the distal end of the shaft in a manner that causes the luminal tissue and an injection orifice to contact each other. This can be done, for example, by a balloon expanding from an opposite side of a shaft relative to an injection orifice to place pressure on luminal tissue located opposite from an injection orifice and to cause the injection orifice to contact adjacent luminal tissue, optionally to produce pressure, strain, or tension on the luminal tissue opposite of the balloon. A mechanical tensioner may be extended from a distal end of a shaft by use of an actuating mechanism such as a mechanical connection between the tissue tensioner and the proximal end of a device, such as at a working shaft proximal end. An inflatable balloon may be extended from a distal end of a shaft by inflating the balloon with pressurized fluid such as air or another gaseous or liquid fluid.

A distal end of a device as described may optionally include a fitting that functions to attach together two or more components of a distal end. Exemplary fittings can be any device or structure that engages and attaches to a distal end of an injection shaft or a working shaft. A fitting can be a component of or attached to another feature as described herein, such as a tissue tensioner, an injection shaft, or a working shaft.

Optionally, a fitting can be attached to an outer surface of an injection shaft or a working shaft; such a fitting can be in the form of a complete or partial ring or cylindrical surface that includes an interior dimension that fits around an outer surface (or portion thereof) of the injection shaft or working shaft. A different exemplary fitting can be in the form of or may include as a component of the fitting, a solid, small diameter rod (diameter approximately that of a working lumen of a working shaft) that extends longitudinally between two components of a distal end, or that extends from one component into another component, e.g., to connect a working shaft to a tissue tensioner assembly. A small diameter rod may be a permanent or removable structure of a tissue tensioner assembly, can extend longitudinally in a proximal direction from the tissue tensioner assembly toward a working shaft, and an enter a distal end (e.g., from a distal end tip) of the working shaft to fit into the working lumen of a working shaft.

Optionally, a surface of an injection shaft or a working shaft can include an opposing or complementary shape, form, or surface, that engages a shape or form of the fitting; examples of complementary or opposing surfaces can include opposing threaded surfaces; opposing snap-fit engagement elements; opposing elements of a mechanical detent engagement, a mechanical spring-engagement; a mechanical key-fit engagement, and the like. Other examples of fittings include opposing press-fit surfaces, and elastic band surfaces. These and like types of fittings can be prepared from plastic or metal materials. Elastic band fittings can be prepared from one or more elastic materials such as rubber (natural or synthetic), elastic polymer, silicone, latex, and the like.

Certain preferred embodiments of fittings can be orientation specific to allow an engagement at only a single orientation, e.g., a fitting may be "keyed. As a single example, a fitting in the form of a cylindrical or partially cylindrical receiver (or receptor) sized to engage a shaft may be keyed (opposing surface structures of the fitting and the shaft may allow engagement in only a single rotational orientation). A keyed fitting can be used to allow an engagement between two attached shaft elements to occur only at a desired orientation between elements of the shafts, e.g.: a fastener that attaches an injection shaft to a working shaft may be keyed to require desired orientation between an injection orifice of the injection shaft and the working shaft, for example to allow viewing of the injection shaft or injection orifice or to require desired positioning of the injection orifice relative to a tissue tensioner associated with the working shaft; alternately a fitting of a tissue tensioner assembly may be keyed to require placement of the tissue tensioner assembly at a desired orientation relative to a working shaft or an injection lumen (and injection orifice).

A fitting can be part of an assembly (e.g., a "fitting assembly") that includes the fitting removably or non-removably attached to another component such as a tissue tensioner, an injection shaft, or a working shaft. An example of a fitting assembly can be a fitting assembly that includes a fitting attached to an injection shaft distal end, wherein the fitting removably attaches to a working shaft. See FIG. 1. The fitting assembly can include one of any of the described fittings attached securely to the injection shaft, and situated to allow the fitting to be attached to a working shaft. Exemplary fittings include an elongate receptor that includes one or more of: threads; a snap-fit engagement; a mechanical detent engagement; a spring; a keyed engagement surface; or an elastic band, capable of being placed on a distal end of a working shaft. In use, the fitting assembly including the injection shaft distal end securely attached to the fitting assembly, can be removably attached to the distal end of the working shaft by attaching the fitting to the working shaft distal end. If desired, the fitting can be keyed to require a determined orientation between the working shaft and the injection shaft. If the fitting is an elastic band, the elastic band can be stretched over a working shaft distal end. Alternately, if the fitting is of a different type, such as a mechanical (threaded, etc.) fitting, the fitting can be attached mechanically. In injection methods, the fitting assembly can be removably attached to a distal end of a working shaft, the working shaft can be placed within a tissue lumen, an optional tissue tensioner can be expanded, fluid can be ejected from the injection shaft to inject tissue, the distal end of the working shaft can be removed from the patient, and the fitting assembly can be removed from the distal end of the working shaft. The working shaft can be re-used in later procedures, and the fitting assembly including the injection shaft may be disposed of or re-used. This embodiment of a fitting assembly can optionally include a tissue tensioner that becomes located about the working shaft distal end when the fitting assembly is placed on the working shaft distal end. See FIGS. 1 through 6.

Another example of a fitting assembly can be a fitting assembly that includes a tissue tensioner (i.e., a tissue tensioner assembly), and attached to a fitting, wherein the fitting can be removably or non-removably attached to an injection shaft distal end. The tissue tensioner assembly can include one of any of the described fittings attached securely to a tissue tensioner, and situated to allow the fitting to be attached to a distal end of a shaft such as a working shaft or an injection shaft. Exemplary fittings include an elongate receptor that includes one or more of: threads; a snap-fit engagement; a mechanical decent engagement; a spring; a keyed engagement surface; or an elastic band; capable of being placed on a distal end of a working shaft or injection shaft. If desired, the fitting can be keyed to require a pre-determined rotational orientation between the tissue tensioner and the working shaft or injection shaft. In use, the fitting of the tissue tensioner assembly can be removably (or non-removably) attached to the distal end of an injection shaft or a working shaft. If the fitting is an elastic band, for example, the elastic band can be placed (e.g., stretched) around the injection shaft distal end. See FIGS. 7A and 7B, showing such a tissue tensioner assembly removably attached to a distal end of an injection lumen.

A tissue tensioner assembly that includes a fitting that can be removably attached to a distal end of a working shaft can, in use, be used according to steps that include: removably attaching the tissue tensioner assembly to a distal end of a working shaft, placing the working shaft (the distal end of the shaft also being associated with an injection shaft) within a tissue lumen, expanding the tissue tensioner, ejecting fluid from an injection shaft associated with the working shaft to inject tissue, and removing the distal end of the working shaft from the patient. The tissue tensioner assembly can be removed from the distal end of the working shaft. The working shaft can be re-used in later procedures, and the tissue tensioner assembly may be disposed of or re-used. In this embodiment, the tissue tensioner assembly may optionally be securely attached to a distal end of an injection shaft and in use the injection shaft becomes disposed adjacent to an exterior surface, and along a length of, the working shaft.

A tissue tensioner assembly that includes a fitting that can be attached (removably or non-removably, such as by adhesive or by integral construction) to a distal end of an injection lumen can, in use, be used according to steps that include: placing the injection shaft within a working lumen of a working shaft such as by loading the proximal end of the injection shaft into the distal end of the working lumen or alternately by loading the distal end of the injection shaft into the proximal end of the working lumen, attaching the tissue tensioner assembly to a distal end of an injection shaft (optionally with the injection shaft already being loaded into the working lumen), placing the working shaft distal end (and injection shaft and tissue tensioner) within a tissue lumen, expanding the tissue tensioner, ejecting fluid from the injection shaft to inject tissue, and removing the distal end of the working shaft (and injection shaft and tissue tensioner assembly) from the patient. The tissue tensioner assembly can be removed from the distal end of the injection shaft; alternately, the entire injection shaft and tissue tensioner assembly can be removed from the working shaft. The working shaft can be re-used in later procedures, and the tissue tensioner assembly, working shaft, or both, may be disposed of or re-used.

Figure 7A:
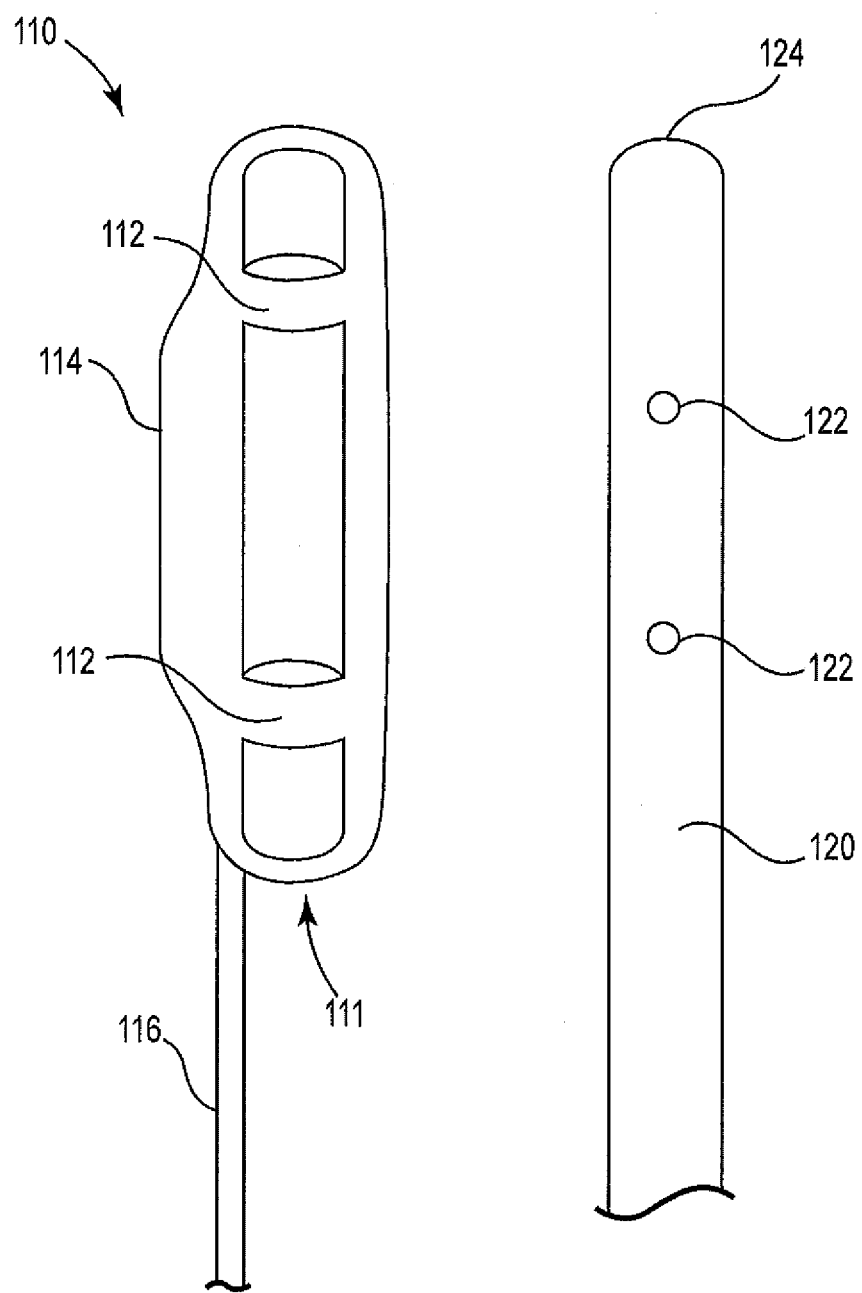
FIGS. 7A and 7B are side views of distal end components of shafts and assemblies as described.
Figure 7B:
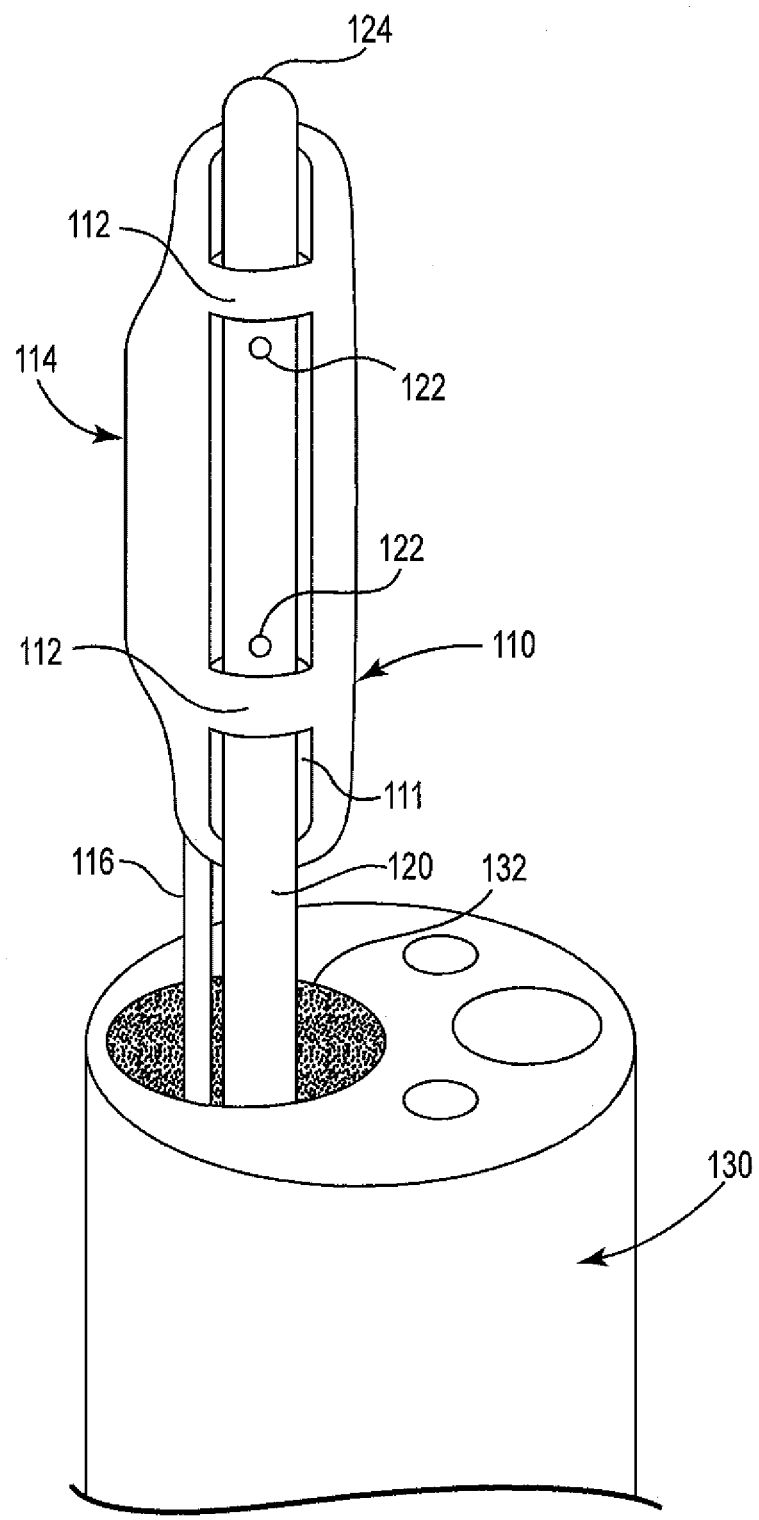

FIGS. 7A and 7B illustrate an embodiment of a tissue tensioner assembly. Assembly 110 includes fastener 111 that includes an elongate receptor sized to receive a distal end of injection shaft 120 (including injection orifices 122 and distal end tip 124). Rings or bands 112 can be elastic or non-elastic, plastic, metal, rubber, etc., bands to removably secure assembly 110 to the distal end of injection shaft 120. Tissue tensioner 114, illustrated as an inflatable balloon in a non-expanded state, is securely attached or optionally integral with fastener 111. Inflation lumen 116 is in fluid communication with tissue tensioner (balloon) 114 in a manner to allow gas or liquid fluid (e.g., air) to be inserted into tissue tensioner 114 to inflate and expand tissue tensioner 114. Optionally a proximal end of inflation lumen 116 can be accessible at the proximal end of a working lumen that can be associated with injection lumen 120 and tissue tensioner assembly 110.

Referring to FIG. 7B, assembly 110 is shown attached to a distal end of injection shaft 120, which is in turn disposed within working lumen 132 of working shaft 130. This distal end configuration comprising injection shaft 120, working shaft 130, and tissue tensioner assembly 110, is an example of a useful side-fire injection shaft configuration movably disposed within a working lumen. Side-firing injection orifices 122 are apposed by tissue tensioner (balloon) 114; when balloon 114 is expanded within a body lumen, side-firing injection orifices 122 are pressured against internal luminal tissue.

Still referring to FIGS. 7A and 7B, tissue tensioner 114 is an inflatable balloon but the tissue tensioner may alternately be of other types, such as an expandable cage. Also, fitting 111 is illustrated to be removable from injection shaft 120, but could alternately be permanent, semi-permanent, or non-removable, or could even be absent in that tissue tensioner 114 could optionally be integral with or otherwise attached to the distal end of injection shaft 120. In still alternate embodiments, inflation lumen 116 could be incorporated into injection shaft 120.

In injection methods, a distal end as shown in FIGS. 7A and 7B can be prepared by attaching the tissue tensioner assembly 110 (removably or permanently) to the distal end of injection shaft 120, as illustrated. The tissue tensioner assembly 110 and injection shaft 120 can be inserted into a distal end of working lumen 132 and passed through working lumen 132 to extend from the distal end of working lumen 132 to a proximal end (not shown) of working lumen 132. Working shaft 130 can be placed within a tissue lumen (e.g., urethra). Tissue tensioner 114 can be expanded to secure placement of injection orifices 122 against internal luminal tissue. Fluid can be ejected from injection orifices 122 to inject tissue. The distal end of working shaft 130 and injection shaft 120 can be removed from the patient. In embodiments wherein fitting 111 is removable, tissue tensioner assembly 110 can be removed from the distal end of injection shaft 120. Working shaft 130 can be re-used in later injection procedures. Injection shaft 120 may be removed from working lumen 132 and may optionally be re-used or discarded.

A needleless fluid delivery system 100 is illustrated generally in FIG. 1 as attached to elastic adapter (i.e., a fitting in the form of an elastic band) 10. The elastic adapter 10 is comprised of compliant or semi-complaint elastic material. The elastic adapter 10 defines a central aperture 12 through which a flexible scope (e.g., a working lumen) is inserted. The elastic adapter 10 has an inner face 14 and an outer face 16 separated by material thickness 18. It is envisioned that the elastic adapter 10 could be disposed about the distal end of a cystoscope, ureteroscope, choledoscope, endoscope or hysteroscope (e.g., any type of working shaft). The amount of elastic tension about the flexible scope may be varied by selecting the thickness and/or type of the elastic material (and the size, e.g., inner diameter, of the elastic adapter). Furthermore, the axial length 20 of elastic adapter 10 may include designated bending areas or areas of greater elastic tension so as not to interfere with the efficiency of the flexible scope. The needless fluid delivery system 100 is attached to the elastic adapter 10 axially at connection region 22. In alternative embodiments it is envisioned that the needless fluid delivery system 100 may be connected by radial bands attached to the outer face 16 of the elastic adapter 10 or is disposed within central aperture 12 of the elastic adapter 10.

Needleless fluid delivery system 100 can comprise an injector (e.g., at a proximal end, not shown), an applicator lumen ("injection lumen") 104, and an injection orifice 102. The injector (e.g., including a console as described herein) can be as simple as manually activated syringe, or can comprise an automated injector including a user interface and a connector member. A connector member at a proximal end or other fluid chamber can include a therapeutic fluid supply and the user interface can comprise an input means for selectively delivering a pressurized fluid through the connector member. Representative input means can include foot pedal, switches, buttons or a touch-screen capable of receiving touch commands as well as displaying system information including a mode of operation as well as operating parameters. The applicator lumen 104 can comprise a non-metal, polymeric tube like device having a proximal attachment end 106 and a distal treatment end (or injection shaft distal end) 108. A non-metal, polymeric tube like device can have a tube length that corresponds to a type of treatment to be performed within a patient's body. For example, when a non-metal, polymeric tube like device is configured to perform a cystoscope or endoscopic procedure, the tube length can range from about 18 to about 72 inches in length. Once the distal treatment end 108, and more specifically, the administration orifice 102 is positioned with respect to the treatment location, the injector can be actuated so as to begin delivery of a therapeutic fluid. In positioning the needless fluid delivery system 100 at treatment location, it will be understood that a medical professional frequently employs a medical imaging system such as, for example, computer axial tomography (CAT), magnetic resonance imaging (MRI), or in the case of treatment of a prostate gland, an exemplary imaging means is transrectal ultrasound (TRUS) so as to achieve the desired position of administration orifice 102. Another imaging means is by direct vision of the distal end of the inserted device, optionally the injection shaft or injection orifice, through direct vision by use of an endoscope.

Figure 2:
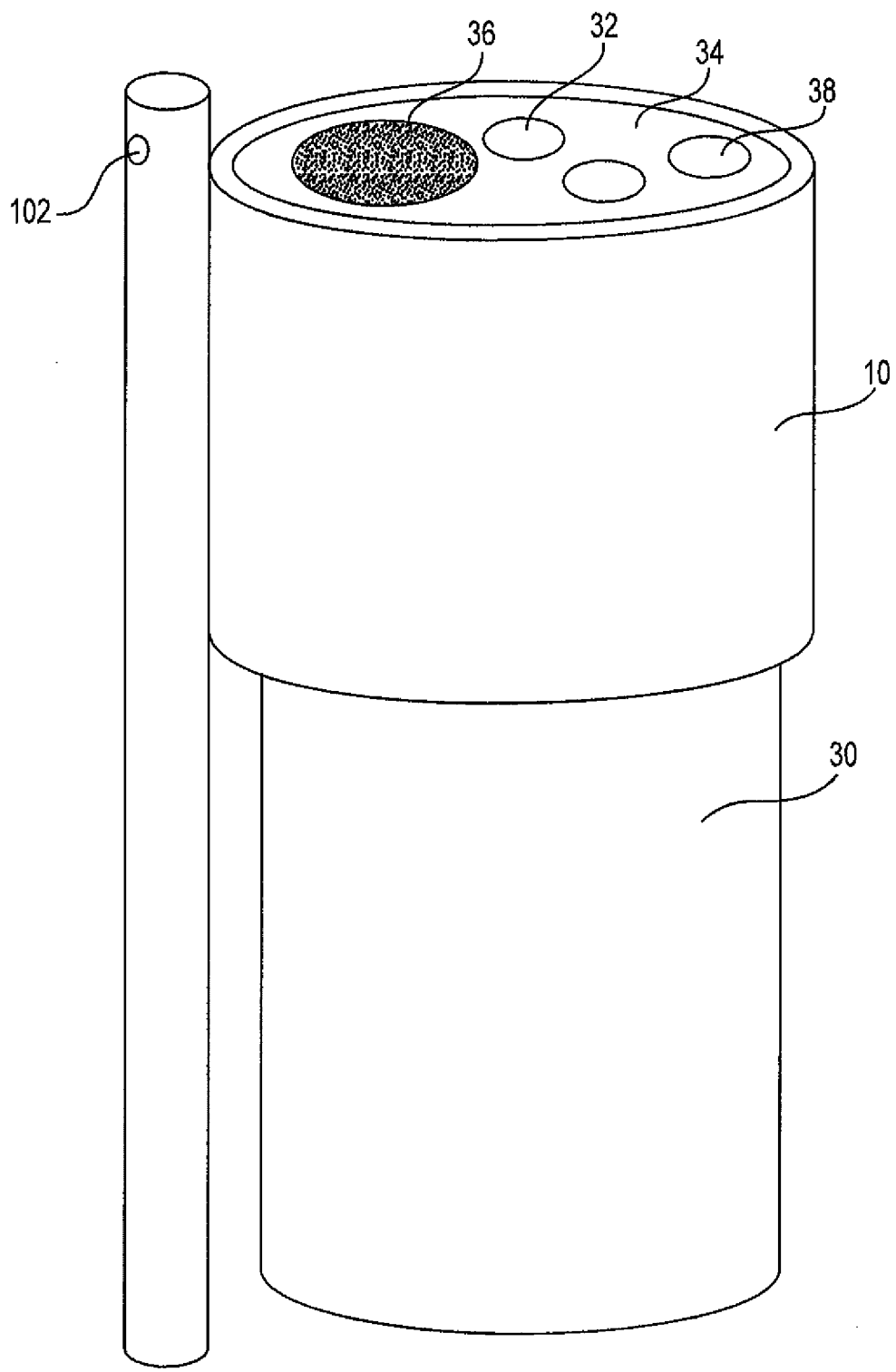
FIG. 2 is a perspective view of an embodiment of an elastic adapter with a therapeutic fluid delivery system disposed about a flexible scope according to the present disclosure.

As illustrated in FIG. 2, elastic adapter 10 is disposed about a flexible scope (e.g., working shaft) 30 such as a cystoscope to deliver therapeutic fluid to a treatment location, such as, for example, the urinary bladder, urethra, prostate, etc. Cystoscope 30 can include a working channel (working lumen) 36, a fiber optic light source 32 and lens 38 such that a medical professional can verify the distal treatment end 34 is positioned proximate the treatment location. It is envisioned that elastic adapter 10 could include an upper face that caps a portion of the distal treatment end 34 of the cystoscope 30. However, any cap portion must be positioned so as not to interfere with the cystoscope operation.

An alternate two-layer embodiment of an elastic adapter (or fitting) 200, is illustrated in FIGS. 3-6. A cystoscope 30 (or other working shaft) is positioned within elastic adapter 200 to deliver therapeutic fluid to a treatment location, such as, for example, the urinary bladder, urethra, prostate, etc. Cystoscope 30 can include a working channel (working lumen) 36, a fiber optic light source 32, and lens 38 such that a medical professional can verify the distal treatment end 34 is positioned proximate the treatment location. Needleless fluid delivery system 100 can comprise an injector (not shown), an applicator lumen ("injection lumen") 104, and an injection orifice 102.

The elastic adapter 200 may be a two layer device so as to include an inflation element 202. An inner elastic sleeve comprises a first layer 204. The first layer 204 is elastically mounted about the distal end 34 of the flexible scope 30. As the flexible scope 30 is stiffer than the elastic adapter 200, the elastic tension created by the stretched elastic adapter does not impinge upon the scope. The second layer 206 is attached around the outer diameter of the first layer 204 to create a balloon 210. A balloon inflation lumen 208 is disposed axially along a central aperture 212 with a first end (proximal end) in communication with a media source such as compressed air or a fluid. A second end 212 of the balloon inflation lumen 208 is in communication with the space between the first layer 204 and second layer 206. It is envisioned that the second layer 206 may radially overlap the axial ends of the first layer 204. The apposition balloon 210 is thus defined by the second layer 206 overlap of the first layer 204.

It is further envisioned that in some embodiments the second layer 206 may only partially surround the first layer 204 as illustrated in FIG. 4. For example, the second layer 206 maybe disposed eccentrically around the first layer 204 leaving an axial section of the first layer 204 exposed. The injection lumen (injection shaft) 104 would thus be attached to the first layer 204 along the exposed section. As the apposition balloon 210 inflates the injection lumen 104 can thus be positioned (within a body lumen). The eccentric geometry allows the apposition balloon 210 to force the injection lumen 104 against the tissue chosen for treatment.

Figure 5:
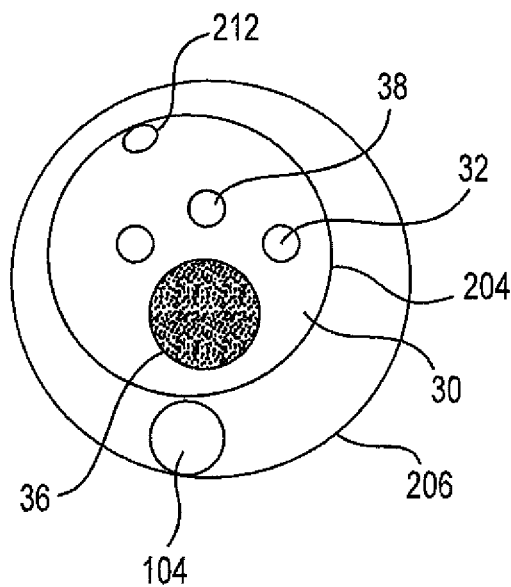
FIG. 5 is another alternate cross sectional view of the present invention.
Figure 6:
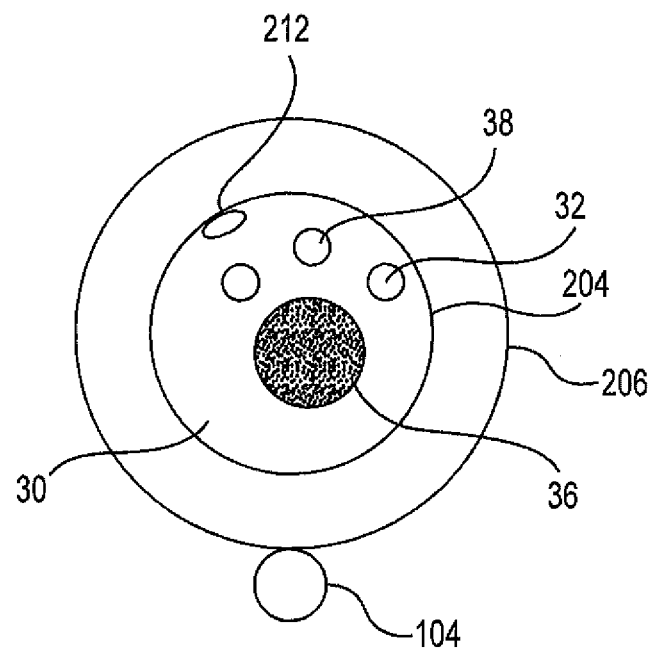
FIG. 6 is another alternate cross sectional view of the present invention.

In an additional embodiment, the injection lumen 104 would be attached between the first layer 204 and second layer 206, as illustrated in FIG. 5 or be attached to the second layer 206 as illustrated in FIG. 6.

In operation, the elastic adapter 200 would be placed about the distal end 34 of the flexible scope 30 by stretching the first layer 204. Elastic tension of the first layer 204 will maintain the position of the needleless injection system 100 relative to the flexible scope 30. The flexible scope 30 would be advanced to a treatment location at which time the balloon 210 would be filled through inflation lumen 212. Selectively inflating balloon 210 will assist in proper positioning of the injection orifice 102. Treatment may include providing a jet-injection of the therapeutic fluid through the injection orifice 102 at a desired treatment site. Generally, a remote injector is utilized to deliver the therapeutic fluid from an external reservoir located at a proximal end of the tube-like device 100. After treatment is complete, the balloon 210 is deflated and the flexible scope 30 withdrawn.

Figure 8:
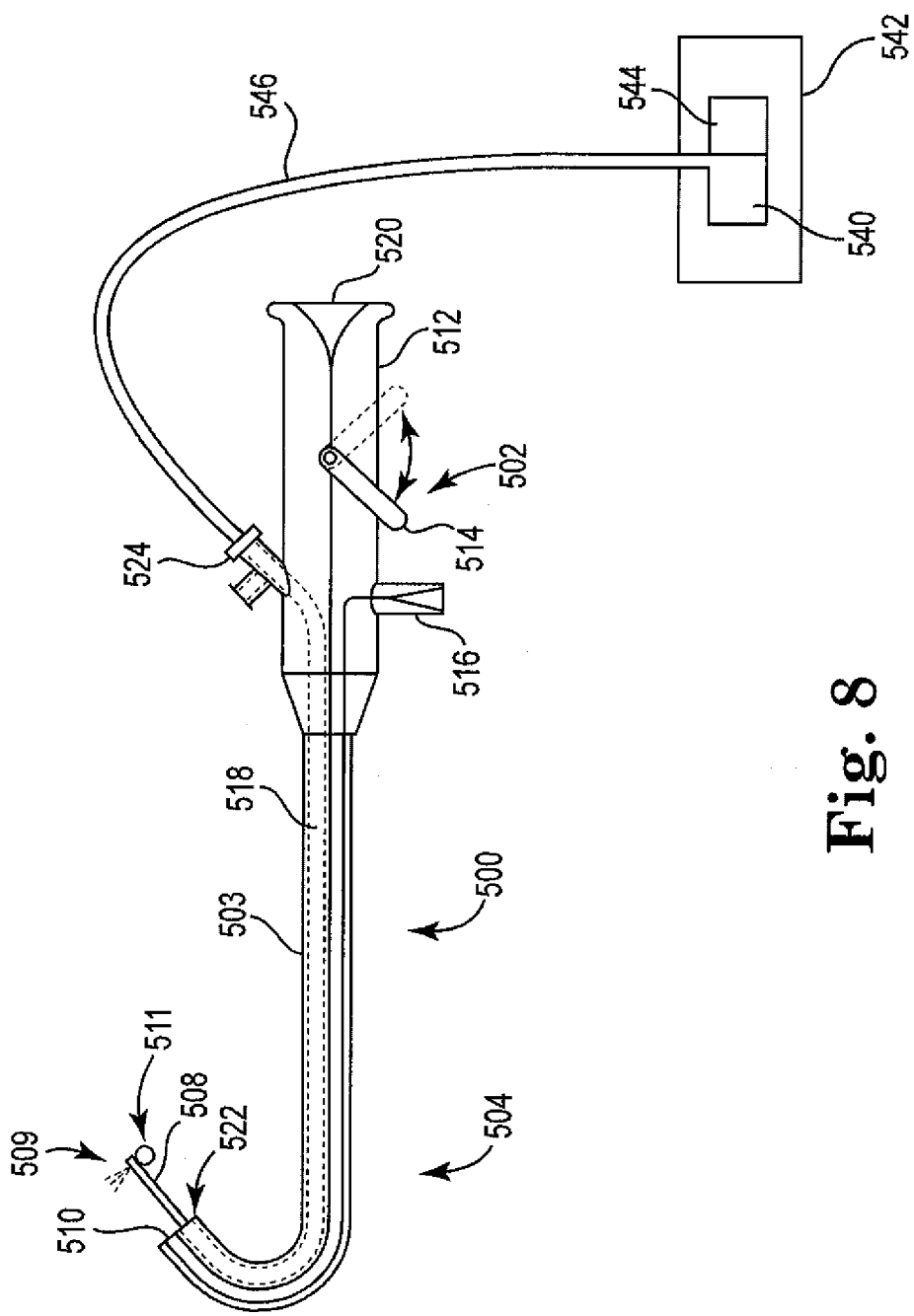
FIG. 8 is an illustration of an exemplary needleless injection system as described.

Another exemplary embodiment of a needleless injection system according to the present description is illustrated at FIG. 8. Device 500 includes a handle 502 and distal shaft end 504 of working shaft 503, which includes injection shaft 508 disposed within working lumen 518. The proximal end of the devices includes handle 502 of a scope that connects to working shaft 503 (e.g., of a cystoscope, endoscope, catheter, or other medical device shaft), including features useful for manipulating or operating features at distal end 504. Handle 502 includes: fiber optic light source 516; steering actuator 514, which can be manipulated to cause the steerable distal end of device 500 to move in at two or more dimensions); viewing lens 520 that allows viewing through fiber optic cable 510; and port 524, which allows for connection of a fluid source to handle 502. Articulation for steering of distal end 504 is indicated in dashed lines.

Still referring to FIG. 8, body 512 connects to working shaft 503, which includes lumens and mechanisms that connect features of proximal end handle 502 to distal end 504. Working lumen 518 is a hollow lumen or channel that extends within working shaft 503 and supports and contains injection shaft 508 in a manner that allows injection shaft 508 to move longitudinally along the length of working shaft 503, to allow the distal end of injection shaft 508 to extend from end opening 522 of working lumen 518. Working shaft 503 also includes fiber optic 510 and a steering mechanism (not shown) that allows steering (deflecting) of distal end 504 by movement of actuator 514. Light source 516 transmits light to distal end 504 by fiber optic 510.

Distal end 504 includes end opening 522 of working lumen 518 from which can be extended injection shaft 508, which includes at least one injection orifice. Also distal end 504 can be steered to allow movement of the tip of working shaft distal end 504, in coordination with extension of injection shaft 508, based on viewing through fiber optic 510, to deliver a fluid with accurate placement at a desired tissue location. The distal end of injection shaft 508 can be any design as described herein, e.g.: can include multiple injection orifices at different length-wise or circumferential locations; can include a tissue tensioner for apposition of an injection orifice against tissue; etc. As illustrated, fluid stream 509 is shown being ejected from an injection orifice (not shown); tissue tensioner (balloon) 511 is located on an opposite side of injection lumen 508 from the injection orifice.

While FIG. 8 illustrates an embodiment of a needleless injection system having an elongate shaft that includes an injection shaft disposed within a working lumen of a working shaft, other embodiments are alternately useful, such as embodiments of distal shaft ends of FIGS. 1 through 6, including an injection shaft dispose on an exterior of a working shaft, and an optional tissue tensioner disposed about a distal end of the working shaft.

Also illustrated at FIG. 8 is shaft 546 extending between port 524 of handle 502 and console 542. Console 542 includes pressure chamber 540 and pressure source 544.

Certain embodiments of tissue tensioner assemblies can include a tissue tensioner, a fitting useful to engage an end of a shaft such as a working shaft, and a fitting ("adapter") useful to engage an end of a lumen assembly. The tissue tensioner can include an inflatable balloon; the fitting can be connected to the tissue tensioner and can also be capable of removably or securely (non-removably) attaching to a shaft such as a working shaft. The adapter can be designed to connect to a second shaft, such as a shaft of a lumen assembly or an injection lumen. The injection lumen can include one or more shaft and one or more lumen, in any configuration, including an inflation shaft that defines an inflation lumen and an injection shaft that defines an injection lumen. The adapter is in fluid communication with an interior space of the inflatable balloon so the lumen assembly can engage the adapter and connect the balloon, through the adapter, through the inflation lumen, to a proximal end of a needleless injection device.

FIGS. 10 through 13D illustrate embodiments of tissue tensioning assemblies and lumen assemblies that can be used with needleless injection devices and systems according to the present description.

Figure 10A:
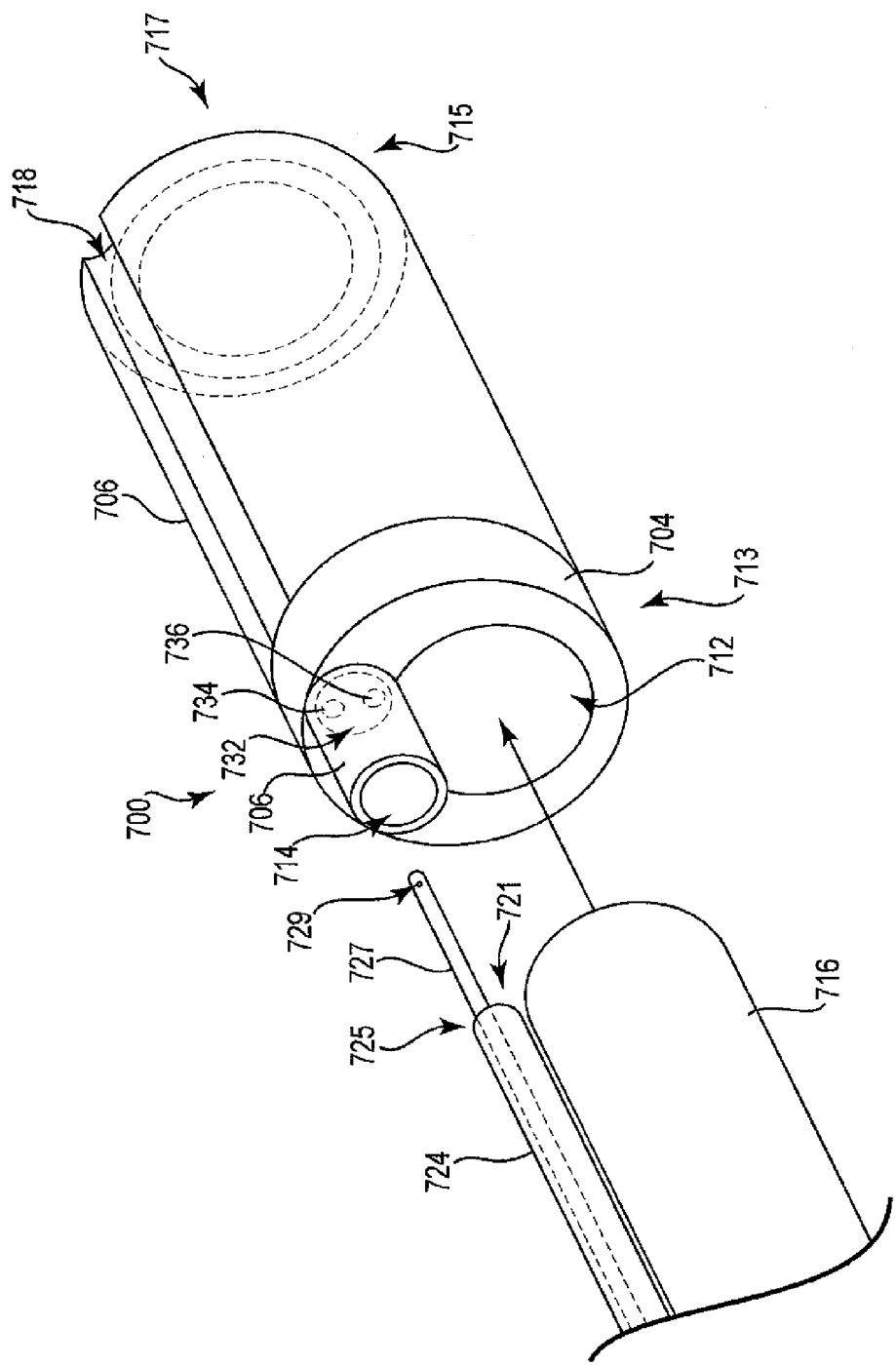
FIG. 10A is a perspective view of an embodiment of a tissue tensioner assembly according to the present disclosure.

Referring to FIG. 10A, tissue tensioner assembly 700 includes an inflatable balloon tissue tensioner that is (optionally and as illustrated) constructed from two pieces that include an inner balloon piece 704 and an outer balloon piece 730. Opening 712 at proximal end 713 is adapted to removably engage and fit over a distal end of a shaft, such as a distal end of a cylindrical working shaft (716 of FIG. 10A). Distal end 715 can also include an opening (717 shown in dashed lines) and the space between the proximal end opening and the distal end opening is configured to engage a distal end of a shaft. Opening 714 at proximal end 713 can be adapted to (removably or securely) fit over a distal end of a lumen assembly (such as a distal end of a lumen assembly 724 at FIG. 10A).

Figures 10B, 10C:
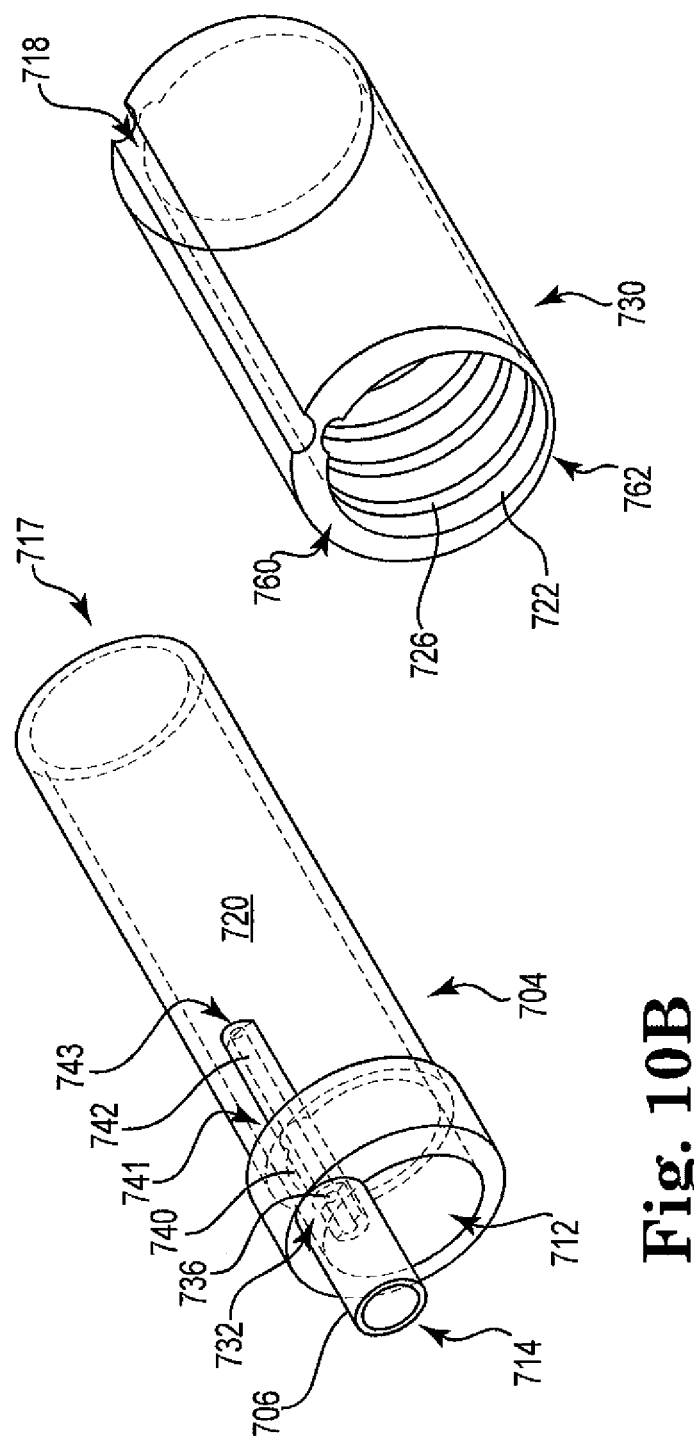
FIG. 10B is a perspective view of an embodiment of an inner piece of a multi-piece tissue tensioner assembly according to the present disclosure.
FIG. 10C is a perspective view of an embodiment of an outer piece of a multi-piece tissue tensioner assembly according to the present disclosure.

Referring to FIGS. 10A, 10B, and 10C, inner balloon piece 704 and outer balloon piece 730 can be assembled into two-piece tissue tensioner assembly 700, by placing inner balloon piece 704 within an interior space of outer balloon piece 730. Adhesive or another type of securement mechanism can be used to maintain the relative positioning of the pieces, for example adhesive can be placed between opposing surfaces at the proximal end, and between opposing surfaces at the distal end of the pieces, to secure the pieces around the circumferences of each end to allow expansion and inflation of the outer balloon piece. Consequently, an inflation fluid (e.g., gas) can be pumped under pressure through an inflation lumen (e.g., held in place at tissue tensioner assembly 700 by adapter 706) and into an interior space (not numbered) located between outer surface 720 of inner balloon piece 704 and inner surface 722 of outer balloon piece 730, to cause expansion of outer balloon piece 730, e.g., for apposition.

A tissue tensioner assembly as described may be prepared by any useful method and from any useful material or materials, specifically including metal or plastic (polymeric) materials, with preferred materials including surgical grade polymeric materials. The materials can be elastomeric and sufficiently stretchable to be deformed and stretched to be adapted to and to fit over an end of a shaft such as a working shaft or a shaft of a lumen assembly or an injection lumen. Specific example of useful biocompatible, materials include polyolefins (e.g., polyethylene, polypropylene) polyacrylates, polyurethane, silicone polymers, natural and synthetic rubbers, latex, vinyl, polyamide ether (e.g., commercially available from Autochem under the trade name Pebax™), and any other relatively inert elastomeric materials. Optionally, with an assembly having a two-piece design, two different materials can be used to construct the assembly, a different material being selected for each of the inner piece and the outer piece, if desired.

According to certain embodiments of tissue tensioning assemblies, an assembly may be constructed of two pieces, one piece that defines an inner portion of a balloon and an adapter, and a second piece that defines an expandable outer portion of a balloon. For example, FIG. 10B illustrates one piece of an exemplary multi-piece construction of a tissue tensioner assembly, inner balloon piece 704. Inner balloon piece 704 includes adapter 706 generally located at proximal end 713 of assembly 700 and non-concentrically positioned relative to the proximal end of the assembly, designed to removably or securely, and in an air-tight fashion, engage a lumen assembly (e.g., distal end of lumen assembly 724).

Adapter 706 is illustrated as a flexible, elastomeric, cylindrical extension on a proximal side of assembly 700 that defines opening (714) sized to engage a distal end of a lumen assembly, such as a tube or tubular shaft. Adapter 706, a deformable, elastomeric cylinder, includes an inner surface that frictionally or non-frictionally engages an outer surface of a lumen assembly that is also optionally and preferably cylindrical. Other types of adapters will also be useful, including any adapter that can maintain engagement between a tissue tensioner assembly and a lumen assembly. Examples of useful engagement structures that may allow engagement between a surface of a tissue tensioner assembly and a surface of a lumen assembly include opposing threaded surfaces, opposing snap-fit engagement elements; opposing elements of a mechanical detent engagement, a mechanical spring-engagement, a mechanical key-fit engagement, and the like.

An adapter (e.g., 706, but also optionally of any other useful design) can engage a lumen assembly and maintain a position of the lumen assembly at a location relative to a tissue tensioner assembly (e.g., 700) such that one or more lumen or lumens of the lumen assembly is in fluid communication with the balloon, or that otherwise places and maintains a position of a lumen or shaft of a lumen assembly at a desired location relative to a tissue tensioner assembly. For example, an adapter can hold a lumen assembly in a position to place an inflation lumen or an opening leading to an inflation lumen at a location of a tissue tensioner assembly that results in fluid communication between the inflation lumen and a balloon of the tissue tensioner assembly to allow inflation of the balloon using pressurized inflation fluid passed through the inflation lumen. Alternately or in addition, an adapter can hold a lumen assembly in a position to place an injection lumen at a position relative to a tissue tensioner assembly that places an injection orifice at a location to eject fluid for injection into tissue, such as opposite a tissue tensioner of the tissue tensioner assembly or opposite a direction of expansion of a tissue tensioner. For example, tissue tensioner assembly 700 includes channel 718 that includes a length-wise depression at an exterior surface of outer balloon piece 730; adapter 706 can hold an injection lumen in place at channel 718 in a manner to position an injection orifice of the injection lumen at a desired location for injecting fluid into tissue, such as opposite of a direction in which a balloon surface of assembly 700 will expand upon inflation.

Generally, a tissue tensioner assembly can include one or more passage, channel, or the like that extends from an adapter useful to engage a lumen assembly, to other locations on the assembly. A passage can function to engage an element of a lumen assembly such as an injection shaft, or a passage can create fluid communication between a space defined by or adjacent to the adapter and an interior space of a balloon. Examples of useful passages of a tissue tensioner assembly are shown, e.g., at FIGS. 10A and 10B.

Referring to FIG. 10A, adapter 706 includes backwall surface 732. Aperture 734 (in dashed lines) (injection lumen aperture) is an aperture that connects to a channel sized to contain an injection shaft. Injection lumen aperture 734 connects to a channel (injection lumen channel) situated generally parallel to a longitudinal axis of tissue tensioner assembly 700 and parallel with (optionally but not necessarily aligned with) a longitudinal axis of a lumen assembly engaged with adapter 706. Accordingly, an injection shaft can extend from a lumen assembly engaged with adapter 706, through aperture 734, and to a location along a length of tissue tensioner assembly 700.

More specifically, as illustrated lumen assembly 724 can be inserted into adapter 706 so that distal end tip 725 of lumen assembly 724 may approach or may abut backwall surface 732. Backwall surface 732 defines two apertures: injection lumen aperture 734 and inflation fluid aperture 736. Injection lumen aperture 734 defines a proximal end of injection lumen channel 740, extending to a distal end at aperture 741 (see FIG. 10B). Injection lumen channel 740 is a channel that can receive and contain injection lumen 727 (having injection orifice 729) of lumen assembly 724 when lumen assembly 724 is engaged with adapter 706. In use, when lumen assembly 724 engages tissue tensioner assembly 700 at adapter 706, injection lumen 727 can be placed within injection lumen channel 740 to locate and secure injection lumen 727 at a position that places injection orifice 729 in a position to inject tissue (i.e., within channel 718) when tissue tensioning assembly 700 is placed in a body lumen of a patient and the tissue tensioning balloon of assembly 700 is inflated.

Inflation fluid aperture 736 defines a proximal end of inflation fluid channel 742 (see FIG. 10B). Inflation fluid channel 742 is channel that aligns with or is at least in fluid communication with an inflation lumen (annular space 721 as illustrated) of lumen assembly 724 when lumen assembly 724 is engaged with adapter 706. Inflation fluid channel 742 extends between proximal aperture 736 and distal aperture 743. In use, when lumen assembly 724 engages tissue tensioner assembly 700 at adapter 706, inflation lumen 721 can be placed adjacent to and in fluid communication with inflation fluid aperture 736 and inflation fluid channel 742 to allow inflation fluid to pass from inflation lumen 721 of lumen assembly 724, through inflation fluid aperture 736, further through inflation fluid channel 742, and into an interior space of an inflatable balloon of assembly 700.

Referring to FIG. 10C, outer balloon piece 730 is shown to include interior surface 722, which defines an expandable outer piece (expandable surface) of a balloon. Interior surface 722 includes ridges or ribs 726 extending around surface 722 in a substantially circumferential manner, which can direct and control a direction expansion of the balloon upon inflation, or prevent adhesion between surfaces (720 and 722) of the balloon.

FIG. 10C also shows optional channel 718, which defines a surface structure useful to maintain a position of a distal end of an injection lumen, especially to locate the injection lumen at a position to place an injection orifice of the injection lumen at a location to inject tissue. Channel 718 is located at a distal end of injection lumen channel 740 so that an injection lumen located to pass through injection lumen channel 740 will become located at channel 718. Channel 718 is located on a side of assembly 700 that does not expand upon inflation of the balloon surface of outer balloon piece 730. Specifically, channel 718 is located at a surface of assembly 700, extends in a length-wise direction parallel to a length-wise axis of assembly 700, on a side of assembly 700 that is opposite the side of assembly 700 that includes a balloon surface that expands when inflated.

As also illustrated at FIG. 10C, a wall configuration (e.g., thickness) of an outer balloon piece may be nonsymmetrical. In specific, upper wall 760 is of greater thickness than lower wall 762. A nonsymmetrical configuration (thickness) can allow different portions of the balloon, around a circumference of the balloon, to expand or to fail to expand upon inflation of the balloon, or to expand at different rates or to different extents. A nonsymmetrical configuration can be accomplished by separating or isolating portions of the balloon wall (e.g., grooves, structures, breaks in the wall, etc.), or by using different wall thickness or different wall materials. As such, the inflation of one side of the respective balloon wall will not undesirably distort the opposing or adjacent side of the balloon. A balloon may expand in a non-symmetrical or asymmetrical manner, either on a length-wise basis (when viewed from a side) or on a radial basis (when viewed from an end, as in FIG. 13D). That is, a balloon may expand a greater distance in one direction (when viewed from an end or a side) compared to the extent of expansion in another direction. In certain embodiments, a balloon can include a one-sided balloon inflation configuration created by bonding the inner balloon piece to the outer balloon piece along a length of the assembly (e.g., on the side where inflation is not desired). It is envisioned that various structure, materials, and techniques can be implemented to achieve the nonsymmetrical and selectively expandable characteristics of the balloon assembly.

A lumen assembly as described can be in the form of a shaft that contains or defines one or more lumen or lumens, preferably at least two lumens that may be arranged in any fashion such as in a concentric configuration, an annular configuration, a side-by-side configuration, or any other useful arrangement. The lumen assembly can include an injection lumen for carrying an injectate from a proximal end to distal end, as well as an injection orifice at the distal end through which the injectate can be ejected at pressure sufficient to penetrate tissue. The lumen assembly can also include an inflation lumen for carrying an inflation fluid from a proximal end to a distal end. The inflation lumen can include an opening at a distal end that can connect to an adapter in a manner that results in fluid communication (through the adapter) between the balloon interior space and the inflation lumen.

A lumen assembly or a constituent inner shaft or outer shaft can be prepared of any useful material. An injection lumen can be constructed from material as described herein, such as a polymeric material capable of withstanding pressure necessary for injection of tissue. An inflation lumen may be made of the same materials, or of materials that are not necessarily capable of withstanding the same pressure. An inflation lumen may be made of a material that may be metal or plastic (polymeric), with preferred materials including surgical grade polymeric materials. The materials can be elastomeric but not necessarily stretchable, and can preferably bend without kinking. Specific example of useful materials include biocompatible polymers such as polyolefins (e.g., polyethylene, polypropylene), polyesters, Nylon, polyester, polyacrylates, silicone polymers, polyurethane, natural and synthetic rubbers, latex, vinyl, polyamide ether (e.g., commercially available from Autochem under the trade name Pebax™), and any other relatively inert elastomeric materials.

Figure 11:
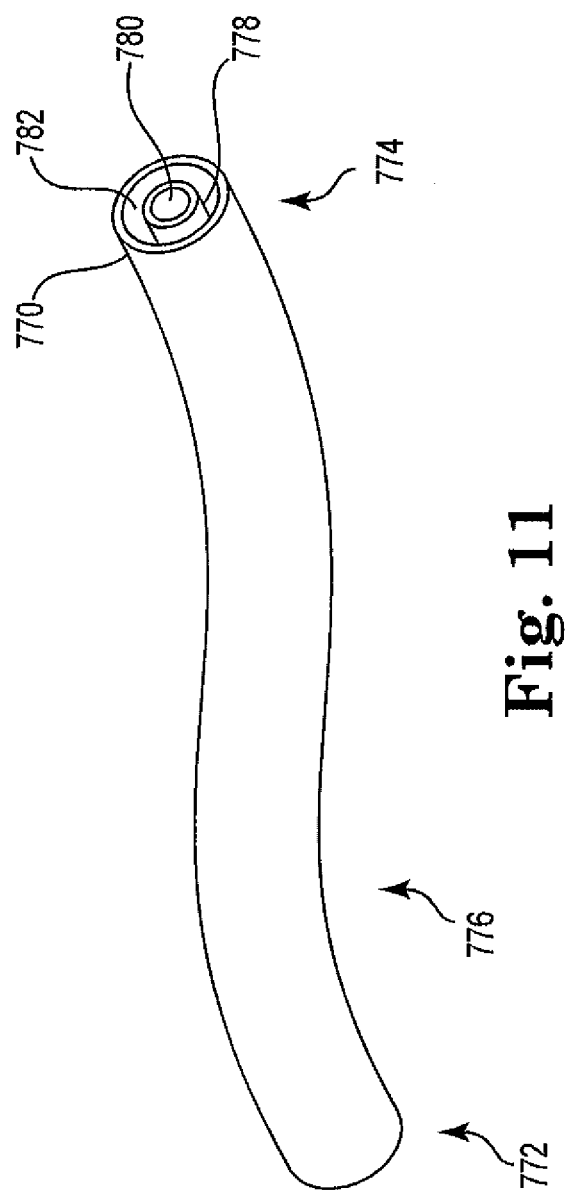
FIG. 11 is a perspective view of an embodiment of a lumen assembly according to the present disclosure.
Figure 12A:
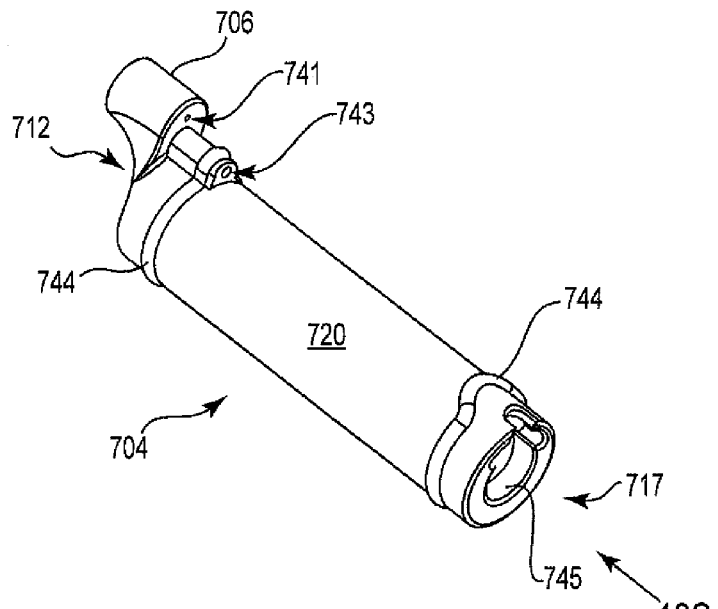
FIG. 12A is a top perspective view of an embodiment of an inner piece of a tissue tensioner assembly according to the present disclosure.
Figure 12B:
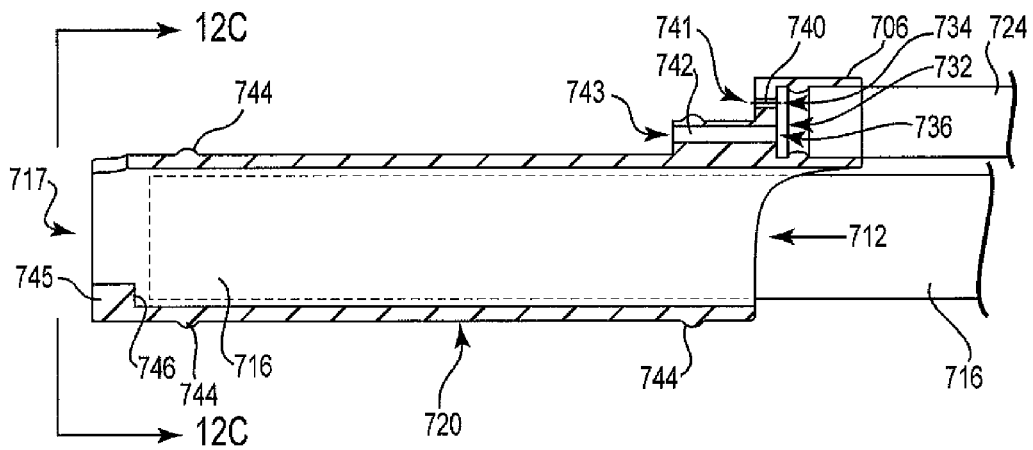
FIG. 12B is a side cut-away view of the piece of FIG. 12A.
Figure 12C:
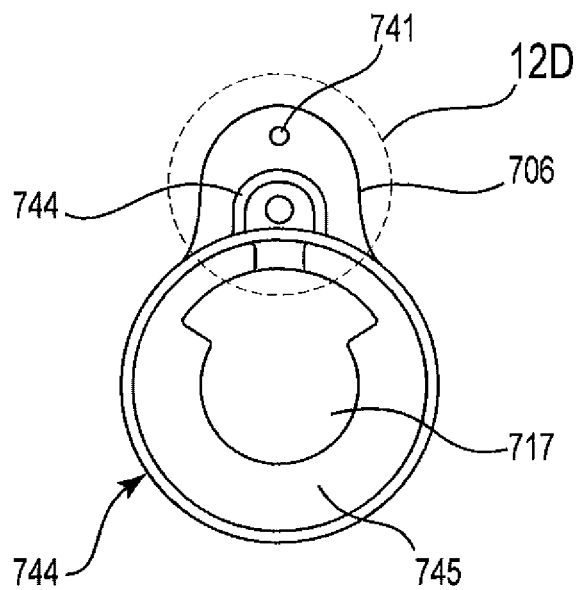
FIG. 12C is an end view of the piece of FIG. 12A.
Figure 12D:
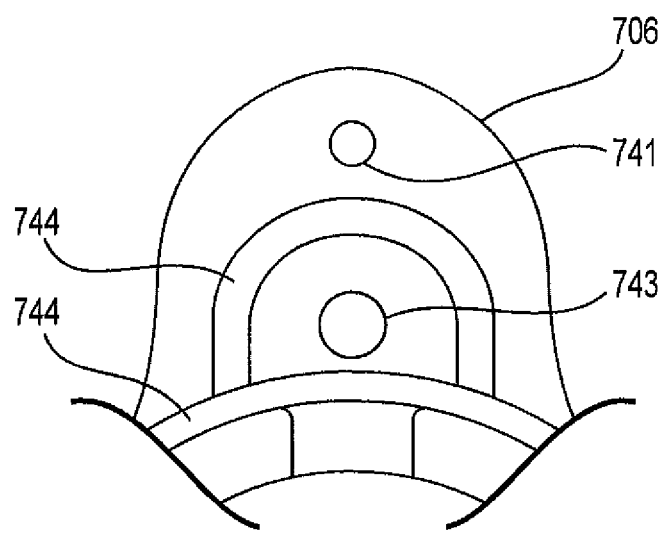
FIG. 12D is a detail end view of the piece of FIG. 12A.
Figure 13A:
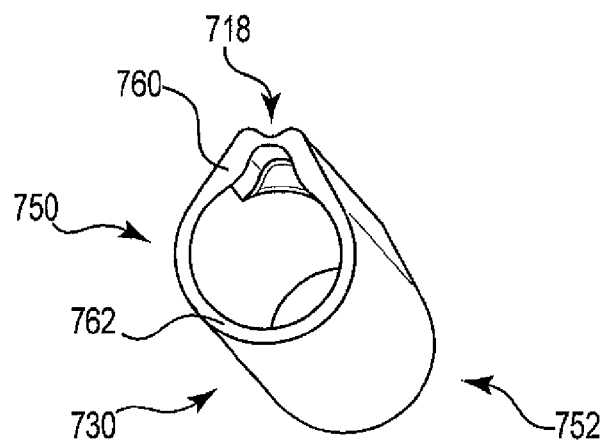
FIG. 13A is a bottom perspective view of an embodiment of an outer piece of a tissue tensioner assembly according to the present disclosure.
Figure 13B:
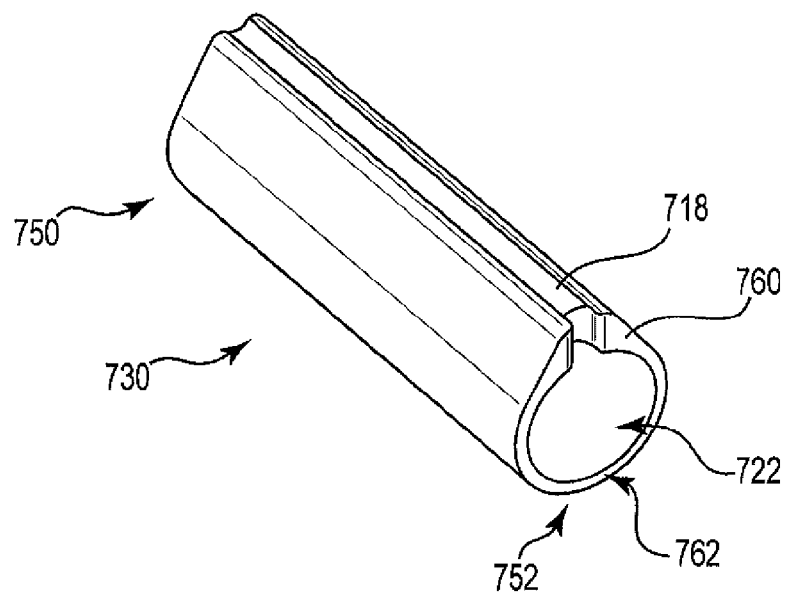
FIG. 13B is a top perspective view of the piece of FIG. 13A.
Figure 13C:
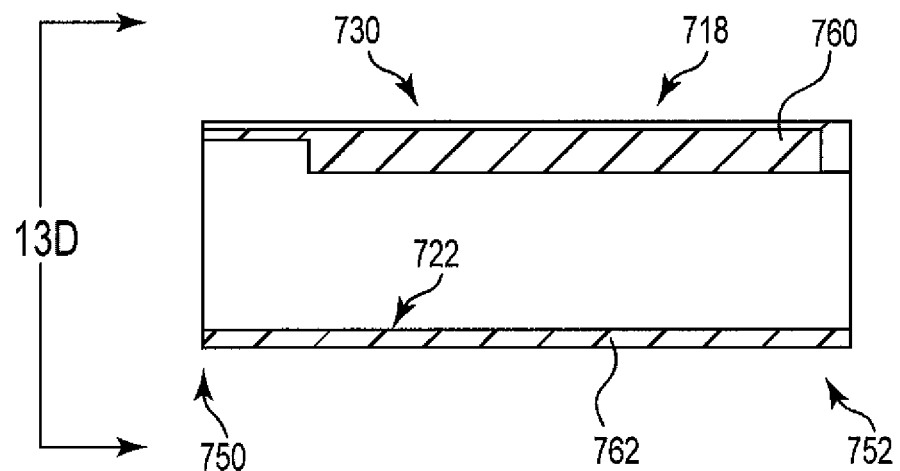
FIG. 13C is a side cut-away view of the piece of FIG. 13A.
Figure 13D:
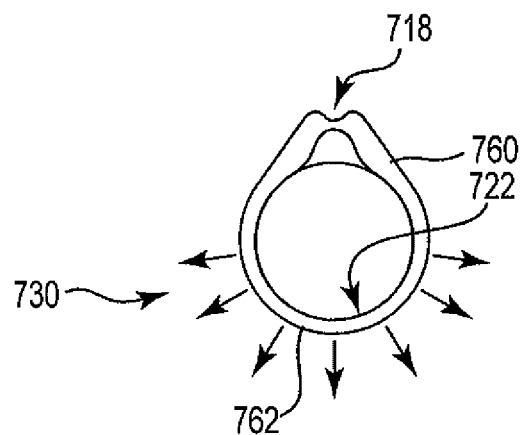
FIG. 13D is an end view of the piece of FIG. 13A.

Referring to FIG. 11, an exemplary lumen assembly can be in the form of two shafts arranged in a "concentric," "coaxial," or "annular configuration. As illustrated to embody this configuration, lumen assembly 776 includes proximal end 772 and distal end 774. Inner shaft 778 functions as an injection lumen and is located within outer shall 770. Injection lumen 780 is defined as the interior space of inject shaft 778. Inflation lumen 782 extends length-wise along the annular space defined between the inner surface of outer shaft 770 and the outer surface of inner shaft 778. Optionally inner shaft 778 can be fixed to prevent lengthwise movement of inner shaft 778 relative to outer shaft 770, or alternately inner shaft 778 can be moveable to allow lengthwise movement of inner shaft 778 relative to outer shaft 770. Distal end 774 can be configured (e.g., sized) to engage an adapter of a tissue tensioner assembly.

According to an alternate embodiment (see lumen assembly 724 at FIG. 10A), inner lumen (e.g., injection lumen) 778 can extend a distance beyond the length of outer lumen 770. Preferably in this embodiment, inner shaft 778 can be fixed to prevent lengthwise movement of inner shaft 778 relative to outer shaft 770. A length of an inner shaft that is greater than a length of an outer shaft may be desired, e.g., to allow the inner shaft and outer shaft to fit an adapter and engage a tissue tensioner in a desired configuration. For example, an outer shaft may be located at and may contact an adapter at a proximal end or proximal side of a tissue tensioner assembly, and an inner (injection) lumen may be designed to extend beyond the adapter to place an injection orifice at a mid or middle (based on length) location or at a distal end or distal side of a tissue tensioner assembly. See FIG. 10A and related text.

FIGS. 12A, 12B, 12C, and 12D illustrate another version of an inner balloon piece 704, slightly modified relative to piece 704 of FIG. 10B. Piece 704 includes features of piece 704 of FIG. 10B, including adapter 706 (to be generally located at proximal end 713 of an assembly 700), designed to removably or securely, and in an air-tight fashion, engage a lumen assembly (e.g., distal end of lumen assembly 724). Adapter 706 is illustrated as a flexible, elastomeric, cylindrical extension on a proximal side of assembly 700 that defines opening (714) sized to engage a distal end of a lumen assembly, such as a tube or tubular shaft. Backwall surface 732 defines two apertures: injection lumen aperture 734 and inflation fluid aperture 736. Injection lumen aperture 734 defines a proximal end of injection lumen channel 740, extending to a distal end at aperture 741. Injection lumen channel 740 is a channel that can receive and contain injection lumen (not shown) of lumen assembly 724 when lumen assembly 724 is engaged with adapter 706. Inflation fluid aperture 736 defines a proximal end of inflation fluid channel 742. Inflation fluid channel 742 extends between proximal aperture 736 and distal aperture 743. Modifications include abutment 745 extending into distal aperture 717, against which a distal end tip of a working lumen will rest when inserted through proximal opening 712 and fitted longitudinally into piece 704; and circumferential ridges 742 to assist engagement with an outer balloon piece, and define an interior space of a balloon for inflation.

FIGS. 13A, 13B, 13C, and 13D illustrate another version of an outer balloon piece 730, slightly modified relative to piece 730 of FIG. 10C. Referring to FIGS. 13A, 13B, 13C, and 13D, outer balloon piece 730 includes interior surface 722, which defines an expandable outer piece (expandable surface) of a balloon. Optional channel 718 defines a surface structured to maintain a position of a distal end of an injection lumen, especially to locate the injection lumen at a position to place an injection orifice of the injection lumen at a location to inject tissue. Channel 718 is located at a distal end of injection lumen channel 740 (at aperture 741) so that an injection lumen located to pass through injection lumen channel 740 will become located at channel 718. Channel 718 is located on a side of assembly 700 that does not expand upon inflation of the balloon surface of outer balloon piece 730. As indicated by the arrows, balloon lower wall 762 is of a smaller thickness compared to upper wall 760. Lower wall 762 expands in a non-symmetrical or asymmetrical manner on a radial basis, expanding a greater distance in a direction away from channel 718, compared to the extent of expansion in other directions.

An alternate tissue tensioner assembly can include a tissue tensioner (e.g., a balloon), an adapter for a lumen assembly, and an alternate fitting or adapter that allows secure or removable attachment of the assembly to a shaft, such as a working shaft or a smaller shaft (e.g., having a diameter of from 0.5 to 2 millimeters) that can extend from the tissue tensioner assembly in a proximal direction and engage a working lumen of a working shaft. For example, a fitting can include or engage with an intermediate mechanical attachment (e.g., a solid, relatively rigid post) that is engaged with or is secured to a working shaft, removably or non-removably. The fitting may be, for example, a post or shaft that engages an aperture of the tissue tensioner assembly at one portion, side, or end, and that engages or is attached to the working shaft (e.g., a working lumen of a working shaft) at a second portion, side, or end.

Figure 14:
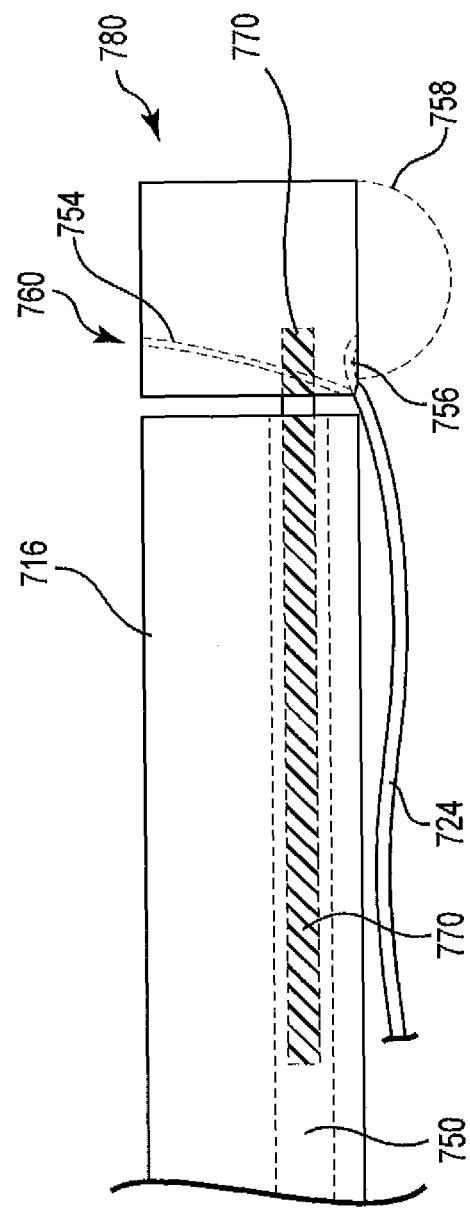
FIG. 14 is a side cut-away view of an embodiment of a tissue tensioner assembly and working shaft.

As an example, FIG. 14 shows a tissue tensioner assembly that includes a tissue tensioner (e.g., a balloon), an adapter for a lumen assembly (e.g., as described herein), and a fitting that includes a post having a first end secured directly or indirectly to the tissue tensioner, and a second end removably engage to a working shaft, e.g., that can be placed within and engaged with a working lumen of the working shaft. The engagement between an end of the post and the working lumen may be any mechanical engagement useful to removably secure the post to the working lumen for use of the needleless injection device, including a frictional engagement, opposing threaded surfaces; opposing snap-fit engagement elements; opposing elements of a mechanical detent engagement, a mechanical spring-engagement, a mechanical key-fit engagement, and the like.

FIG. 14 illustrates an embodiment of a needleless injection device that includes working shaft (e.g., cystoscope) 724 and tissue tensioner assembly 780. Working shaft 724 includes working lumen 750. Tissue tensioner assembly 780 is illustrated schematically as a generic block structure that can take on any form, shape, or size, etc., useful to support the structures presently described. For example, assembly 780 may include an open cylindrical ring or partial ring structure, or other open structure, that allows placement of an injection orifice at one location of the ring and a tissue tensioner (e.g., balloon) that can expand in the opposite direction, while still allowing other optional functionality of a working shaft (e.g., cystoscope) such as viewing of the injection lumen. A distal end of post 770 engages assembly 780 in a permanent or a removable manner, e.g., by engaging an elastic aperture (not shown) in assembly 780. The elastic lumen can have a diameter suitable to securely or removably engage the outer surface of post 780, and an depend on the diameter of post 780; examples of suitable diameters of a post and an elastic lumen can be from 0.5 to 2 millimeters.

Exemplary tissue tensioner assembly 780 engages a post 770, permanently or removably. In one embodiment, assembly 780 can includes an adapter (e.g., comprising an elastic aperture, not specifically shown) as described herein, capable of engaging a distal end of lumen assembly 724, which includes an injection lumen and an inflation lumen. Tissue tensioner assembly 780 also includes inflatable balloon 758, inflation fluid channel 756, orifice 760, and channel 754. Channel 754 can be adapted to contain an injection lumen to allow the injection lumen to extend from an lumen assembly 724 to aperture 760, where an injection orifice of the injection lumen can be placed for tissue injection (similar to the configurations of FIGS. 10A, 10B, and 12A, 12B). Alternately (and as illustrated) channel 754 can constitute a pressure resistant extension of an injection lumen connected to an injection lumen of lumen assembly 724, and orifice 760 be an injection orifice.

Post 770 extends from tissue tensioner assembly 780 and engages working lumen 750, preferably in a removable configuration. Accordingly, post 770 and the assembly of post 770 with tissue tensioner assembly 780 are selectively attachable to the working shaft (e.g., endoscope device) 716 rather than integrally formed. The structure by which assembly 780 is attached to shaft 716 is post (rod or tube) 770, or another like attachment mechanism, configured for selective attachment into working lumen 750. Various size and dimensional configurations are available for the post 770 and working lumen 750 interconnection. For instance, the post 770 can include geometrical features, e.g., axial slots, tapered profile, or a soft outer material to facilitate press fitting of the post 770 within working lumen 750. In various embodiments, the post 770 and lumen 750 interconnection can be configured such that fluid is still permitted to flow through the lumen 750. The embodiment of FIG. 14 enables use of the working shaft 716 with the high-pressure delivery device without attaching the delivery device or to the outside of the scope, and without running the delivery lumen along the entire length of the working channel of the endoscope.

With any of the above features of fluid delivery devices, a device could include an electronic process control system that can be programmed to make fluid deliveries having various locations, volumes, and other injection properties such as depth and degree (e.g., shape and distance) of dispersion and size of particles of fluid.

A needleless injection system can be use to perform treatment methods by steps that include one or more of the following: providing a needleless injection device substantially as described herein; inserting a distal end of a shaft of the fluid delivery device into a patient, e.g., through the meatus and into the urethra; navigating the distal end until an injection orifice at the distal end of the shaft is positioned at a desired delivery site. An injection shaft distal end can be positioned with a sidewall in contact with tissue, with a longitudinal axis of the shaft in line with (e.g., parallel to) tissue; an optional tissue tensioner can be used to cause a sidewall of the injection shaft distal end to contact and be pressed against the tissue surface to cause an injection orifice to contact the tissue surface for injection.

By any of the described methods, multiple injection orifices can provide the ability to place one or more different fluids at multiple locations of the urethra, prostate, bladder, or bladder neck, or other tissue, etc. Other treatment locations can include a rectal treatment location, a gastrointestinal treatment location, a nasal treatment location, a bronchial treatment location, or an esophageal treatment location. Features of devices described herein, such as optical features, steerable shafts, tissue tensioners, and the ability to deliver multiple different types of fluid, allow for improved control over the location of injection or instillation of a fluid.

According to certain exemplary fluid delivery procedures of the invention, fluid such as ethanol or a biologically active agent can be delivered to the bladder, urethra, prostate, or bladder neck, etc., in a manner that causes the fluid to be injected into the tissue using a needleless delivery orifice.

Devices of the present description can be useful to treat of various tissues, including of the urinary tract, in females or males. For example, devices as described may be useful to inject the bladder, bladder neck, the urethral tissue itself or the external sphincter, or for transurethral injection of the prostate in a male. In other embodiments, a fluid may be injected into tissue of the urinary tract (e.g., bladder, urethra, kidneys, ureters, prostate, etc.) such as individual or combination treatments using drugs or other therapeutic agents, e.g., botulinum toxin ("botox"), an antiandrogen, a neurotoxin, among others as will be understood. One advantage of injection of an active pharmaceutical agent at a location of use is the placement of the agent to avoid systemic side effects. Specific examples of active pharmaceutical agents that may be injected include botulinum toxin types A through G; 5-alpha reductase inhibitors such as dutasteride and finasteride; alpha blockers such as alfuzosin, doxazosin, prazosin, tamsulosin hydrochloride, terazosin, ethanol, to treat BPH; or any of various antibiotics (e.g., to treat prostatitis) and analgesics.

Figure 9:
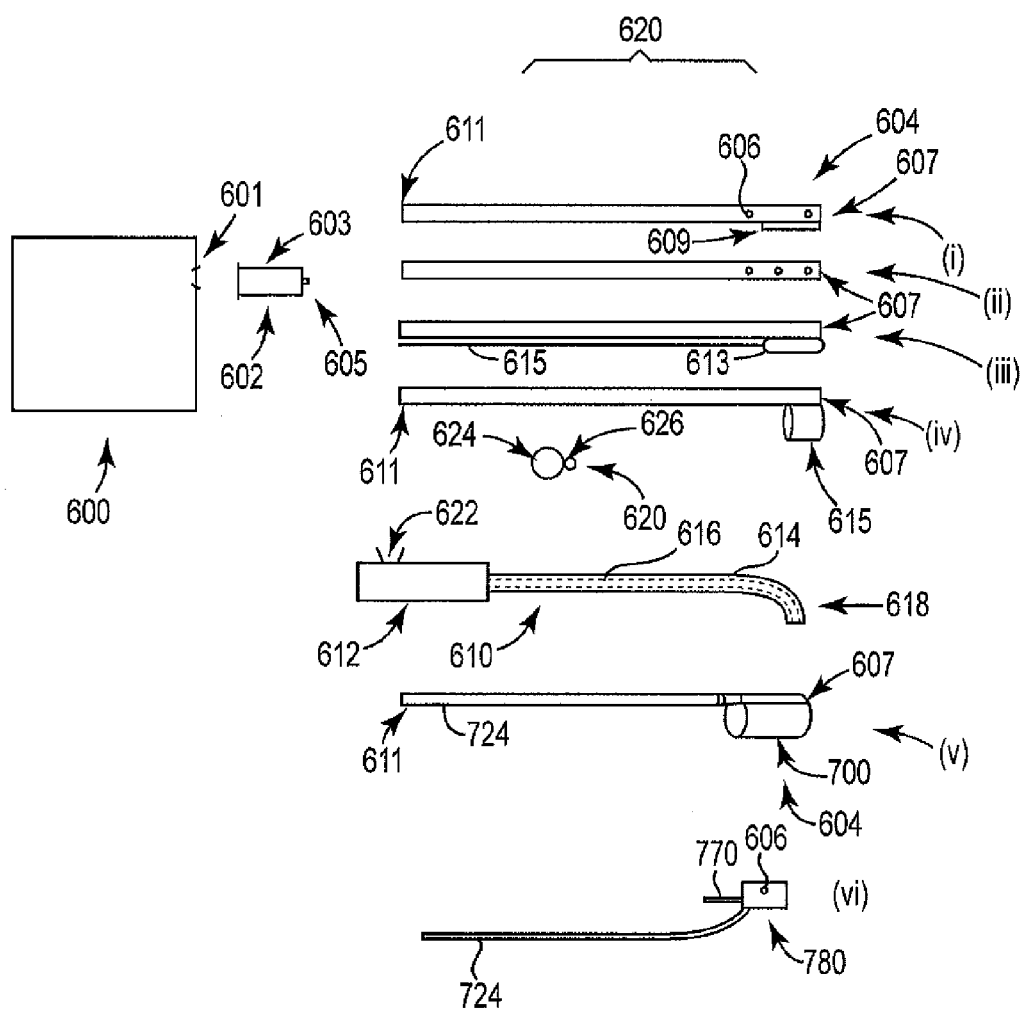
FIG. 9 illustrates options of combinations of systems as described.

FIG. 9 illustrates components of combination 620 of the invention. Any different combination of components can be included in a system or set. The components include console 600, optional "connector member" or external, removable pressure chamber 602, multiple varieties of injection shaft attachments (i) through (iv) that can be separately attached to console 600 or removable pressure chamber 602, and a single working shaft 610 including handle 612. Console or console housing 600 can be as described, and includes at least a pressure source. Port 601 allows connection to optional removable pressure chamber 602, which can be connected at a proximal end to port 601, and has distal end 605 that can be connected to a proximal end of an injection shaft attachment. Optional port 603 of pressure chamber 602 can be used to insert fluid into pressure chamber 602. Each of injection shaft attachments (i), (ii), (iii), (iv), (v), and (vi), is exemplary and for purposes of illustration of exemplary combinations. Each includes a proximal end (611) that can removably attach to console or console housing 600, optionally by removably attaching to connector member 602 at distal end 605. Each injection shaft attachment also includes one or more injection orifice 606 at a distal end 604, connected through an inflation lumen (not shown, or included at lumen assembly 724 of attachment (v)) to the proximal end. Each injection orifice as illustrated is on a proximal side of a distal end tip 607.

An optional component of combination 620 is working shaft 610, which may be as described herein, e.g., including handle 612, port 622 suitable to introduce an injection shaft into working lumen 616 of working shaft 614, optional steerable distal end 618, and an optional optical feature (not shown).

Another optional component of a combination 620 can be a fastener assembly 620 having fastener 624 (e.g., an elastic fastener or other form of elongate receptor, optionally keyed) capable of attaching to a distal end of working shaft 624, and another fastener 626 (e.g., an elastic fastener or other form of elongate receptor, optionally keyed) capable of attaching to a distal end of an injection shaft.

A combination can include any one or combination of injection shaft attachments as shown or otherwise described herein. An exemplary injection shaft attachment can include any one or more of: a side-fire distal end with an elongate receptor 609 that may be an elongate elastic receptor or a non-elastic elongate receptor capable of attaching to an outside surface of working shaft distal end 618, and that is also removably attached to distal end 604 (i); a side-fire distal end with an optional malleable distal end feature (not shown) and multiple injection orifices along a length of the distal end (ii); a distal end with a single injection orifice near distal end tip 607, including tissue tensioner (e.g., inflatable balloon) 613 attached (e.g., securely) to the injection shaft distal end on the side opposite the injection orifice, and inflation lumen (or mechanical actuator, if the tissue tensioner is mechanically actuated) 615 extending alongside the injection shaft to a proximal end (iii); and, a distal end with a single injection orifice near distal end tip 607, including combined fitting and tissue tensioner 615 attached (e.g., securely) to the injection shaft distal end on the side opposite the injection orifice, an inflation lumen (not shown) extending alongside or within the injection shaft to a proximal end, and the combined fitting and tissue tensioner being an elastic or non-elastic fitting sized to fit at the distal end 618 of working shaft 614.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

The invention claimed is:

1. A tissue tensioner assembly comprising a tissue tensioner, a fitting, and an adapter, in combination with a lumen assembly, the tissue tensioner assembly having a distal end, a proximal end, and a length extending between the distal end and the proximal end,
   the tissue tensioner comprising an inflatable balloon along a portion of the length of the tissue tensioner assembly,
   the fitting being connected to the tissue tensioner along a portion of the length and comprising an opening at the proximal end and an inner space defined by an inner surface extending distally from the opening, the fitting being capable of attaching to a distal end of a shaft by passing the opening over the distal end of the shaft and placing the distal end within the inner space, and
   the adapter being non-concentrically positioned relative to the fitting at the proximal end of the assembly and connected to a distal end of the lumen assembly, the lumen assembly comprising an inflation lumen and an injection lumen, wherein the adapter comprises a backwall surface through which an inflation lumen aperture and an injection lumen aperture extend for communication with the inflation lumen and the injection lumen, respectively, wherein the adapter is in fluid communication with an interior of the inflatable balloon, and the inflation lumen is in fluid communication with the adapter, and
   wherein the injection lumen comprises an injection orifice located along the length of the tissue tensioner assembly.

2. A tissue tensioner assembly according to claim 1 wherein the fitting is capable of engaging an elongate shaft having an outer dimension in a range from 4 to 10 millimeters, the fitting inner surface having an inner dimension in a range from 4 to 10 millimeters.

3. A tissue tensioner assembly according to claim 1 wherein the fitting comprises an elongate receptor comprising one or more of: an elastic band, a detent, spring-engagement, a snap-fit engagement, a press-fit engagement, a threaded engagement, a key-fit engagement, an elastic aperture, and combinations of these.

4. A tissue tensioner assembly according to claim 1 wherein the shaft is a post and the fitting engages the post.

5. A tissue tensioner assembly according to claim 1 wherein the lumen assembly comprises a tubular inner shaft and a tubular outer shaft, the injection lumen is located at an interior of the tubular inner shaft and comprises the injection orifice at a distal end, and the inflation lumen is located at an annular space between the tubular inner shaft and the tubular outer shaft.

6. A tissue tensioner assembly according to claim 1 wherein the inflatable balloon is capable of expanding asymmetrically relative to a longitudinal axis of the shaft measured at the distal end of the shaft.

7. The tissue tensioner assembly of claim 1 in combination with a working shaft comprising an endoscope, wherein the fitting is separable from a working shaft distal end and can be placed at the working shaft distal end at an outside surface of the working shaft distal end.

8. The tissue tensioner assembly in combination with the shaft of claim 1 wherein the lumen assembly is separable from a working shaft.

9. The tissue tensioner assembly of claim 1 wherein the adapter comprises an elastic band and the inflatable balloon is connected to the elastic band.

10. A tissue tensioner assembly comprising:
    a tissue tensioner comprising an inflatable balloon;
    a fitting connected to the tissue tensioner and attachable to a shaft;
    an adapter being non-concentrically positioned relative to the fitting and in fluid communication with an interior of the inflatable balloon; and
    a lumen assembly engaged with the adapter, the lumen assembly comprising an inflation lumen and an injection lumen, the inflation lumen being in fluid communication with the interior of the inflatable balloon, and the injection lumen being in fluid communication with an injection lumen orifice,
    wherein the adapter comprises a backwall surface through which an inflation lumen aperture and an injection lumen aperture extend for communication with the inflation lumen and the injection lumen, respectively, and
    wherein the injection lumen orifice is adjacent to the adapter and connected to an injection lumen channel, wherein a first length of injection lumen engages the injection lumen channel, and wherein a second length of injection lumen extends past the injection lumen channel to be located on a distal side of the injection lumen channel and at an exterior of the tissue tensioner assembly with the injection orifice exposed.

11. A tissue tensioner assembly according to claim 10 wherein the fitting is capable of engaging an elongate shaft having an outer dimension in a range from 4 to 10 millimeters, the fitting having an inner surface having an inner dimension in a range from 4 to 10 millimeters.

12. A tissue tensioner assembly according to claim 10 wherein the fitting comprises an elongate receptor comprising one or more of: an elastic band, a detent, spring-engagement, a snap-fit engagement, a press-fit engagement, a threaded engagement, a key-fit engagement, an elastic aperture, and combinations of these.

13. A tissue tensioner assembly according to claim 10 wherein the lumen assembly comprises a tubular inner shaft and a tubular outer shaft, the injection lumen is located at an interior of the tubular inner shaft and comprises the injection orifice at a distal end, and the inflation lumen is located at an annular space between the tubular inner shaft and the tubular outer shaft.

14. The tissue tensioner assembly of claim 10 in combination with a working shaft comprising an endoscope, wherein the fitting is capable of being removably attached to a working shaft distal end by passing the opening over the working shaft distal end and placing the working shaft distal end within an interior space.

15. The tissue tensioner assembly of claim 14 wherein the lumen assembly is separable from the working shaft.

16. The tissue tensioner assembly of claim 10 wherein the lumen assembly is separable from the tissue tensioner assembly.

17. A tissue tensioner assembly comprising:
- a tissue tensioner comprising an inflatable balloon at a lengthwise location along a length of the tissue tensioner assembly;
- a fitting connected to the tissue tensioner and being capable of attaching to a shaft and including an elastic band; and
- an adapter, in combination with a lumen assembly, the adapter being non-concentrically positioned relative to the fitting, and connected to the lumen assembly, the lumen assembly comprising an inflation lumen and an injection lumen, wherein the adapter comprises a backwall surface through which an inflation lumen aperture and an injection lumen aperture extend for communication with the inflation lumen and the injection lumen, respectively,
- wherein the adapter is in fluid communication with an interior of the inflatable balloon,
- wherein the injection lumen comprises an injection orifice located at the lengthwise location of the tissue tensioner assembly, and
- wherein the inflatable balloon is connected to the elastic band.

* * * * *